(12) United States Patent
Hegg et al.

(10) Patent No.: US 9,194,800 B2
(45) Date of Patent: Nov. 24, 2015

(54) SYSTEMS, DEVICES, AND METHODS EMPLOYING ANGULAR-RESOLVED SCATTERING AND SPECTRALLY RESOLVED MEASUREMENTS FOR CLASSIFICATION OF OBJECTS

(71) Applicant: Tokitae LLC, Bellevue, WA (US)

(72) Inventors: Michael C. Hegg, Seattle, WA (US); Benjamin K. Wilson, Kirkland, WA (US)

(73) Assignee: Tokitae LLC, Bellevue, WA (US)

( * ) Notice: Subject to any disclaimer, the term of this patent is extended or adjusted under 35 U.S.C. 154(b) by 498 days.

(21) Appl. No.: 13/662,724

(22) Filed: Oct. 29, 2012

(65) Prior Publication Data
US 2014/0118555 A1    May 1, 2014

(51) Int. Cl.
*H04N 5/225* (2006.01)
*G01N 21/47* (2006.01)
*G01N 21/51* (2006.01)
*G06K 9/00* (2006.01)

(52) U.S. Cl.
CPC .............. *G01N 21/474* (2013.01); *G01N 21/51* (2013.01); *G06K 9/00127* (2013.01)

(58) Field of Classification Search
CPC .. G01N 21/474; G01N 21/51; G06K 9/00127
See application file for complete search history.

(56) References Cited

U.S. PATENT DOCUMENTS 5,832,931 A * 11/1998 Wachter et al. ............... 128/898
5,991,028 A    11/1999 Cabib et al.
6,271,916 B1 * 8/2001 Marxer et al. ............... 356/237.3
6,680,377 B1 * 1/2004 Stanton et al. ............... 536/22.1
2001/0045529 A1 * 11/2001 Iketaki et al. ............... 250/493.1
2002/0031249 A1 * 3/2002 Komuro et al. ............... 382/149
2002/0097388 A1 * 7/2002 Raz .................................. 356/39
2002/0119826 A1 * 8/2002 Matsuda et al. ............... 472/60
2003/0141459 A1 * 7/2003 Hegazi et al. ............... 250/461.1
2004/0125372 A1 * 7/2004 Walla et al. .................... 356/318
2004/0188620 A1 * 9/2004 Servaites et al. ......... 250/339.15
2005/0001155 A1 * 1/2005 Fergason ....................... 250/221
2005/0265586 A1   12/2005 Rowe et al.
2006/0209171 A1 * 9/2006 Shiraishi ....................... 347/259

(Continued)

FOREIGN PATENT DOCUMENTS

WO    WO 2012/012800 A2    1/2012

OTHER PUBLICATIONS

PCT International Search Report; International App. No. PCT/US2013/067025; Mar. 18, 2014; pp. 1-2.

*Primary Examiner* — Jay Au Patel
*Assistant Examiner* — Joseph Suh

(57) ABSTRACT

Systems, devices, and methods are described for identifying, classifying, differentiating, etc., objects. For example a hyperspectral imaging system can include a dark-field module operably coupled to at least one of an optical assembly, a dark-field illuminator, and a hyperspectral imaging module. The dark-field module can include circuitry having one or more sensors operable to acquire one or more dark-field micrographs associated with scattered electromagnetic energy from an object interrogated by the dark-field interrogation stimulus. The hyperspectral imaging module can be operably coupled to the dark-field module, and can include circuitry configured to generate an angular-resolved and spectrally resolved scattering matrix based on the one or more dark-field micrographs of the object.

27 Claims, 13 Drawing Sheets

(56) References Cited

U.S. PATENT DOCUMENTS

| | | | |
|---|---|---|---|
| 2007/0141819 A1* | 6/2007 | Park et al. | 438/584 |
| 2007/0184373 A1* | 8/2007 | Mertens | 430/65 |
| 2007/0229823 A1* | 10/2007 | Sung et al. | 356/336 |
| 2008/0151223 A1* | 6/2008 | Treado et al. | 356/73 |
| 2009/0127474 A1* | 5/2009 | Tsuneta et al. | 250/442.11 |
| 2009/0281753 A1* | 11/2009 | Noy | 702/81 |
| 2009/0326614 A1* | 12/2009 | El-Sayed et al. | 607/88 |
| 2010/0027003 A1* | 2/2010 | Cappel | 356/317 |
| 2010/0102784 A1 | 4/2010 | McDonald et al. | |
| 2010/0222774 A1 | 9/2010 | Hegg et al. | |
| 2010/0246927 A1 | 9/2010 | Arbuckle | |
| 2011/0085162 A1* | 4/2011 | Verstappen et al. | 356/237.5 |
| 2011/0222059 A1 | 9/2011 | Behrend et al. | |
| 2011/0255753 A1 | 10/2011 | Levenson et al. | |
| 2012/0200694 A1* | 8/2012 | Garsha et al. | 348/79 |
| 2012/0201533 A1* | 8/2012 | Gariepy et al. | 398/26 |
| 2012/0225475 A1* | 9/2012 | Wagner et al. | 435/288.7 |
| 2012/0258549 A1* | 10/2012 | Lu et al. | 436/501 |
| 2012/0274931 A1* | 11/2012 | Otani et al. | 356/237.3 |
| 2012/0276549 A1* | 11/2012 | Cunningham et al. | 435/7.1 |
| 2014/0049779 A1* | 2/2014 | Tin et al. | 356/456 |

\* cited by examiner

Fig. 8

802 one or more instructions for focusing electromagnetic energy onto at least one focal region, at one or more angles of incidence relative to an optical axis of an optical assembly one or more instructions for acquiring one or more angular-resolved and spectrally resolved dark-field images of the object one or more instructions for generating angular-resolved and spectrally resolved hyperspectral information representation based on the one or more angular-resolved and spectrally resolved dark-field images of the object one or more instructions for classifying objects in the object responsive to a comparison of the angular-resolved and spectrally resolved hyperspectral information representation to reference angular-resolved and spectrally resolved hyperspectral information one or more instructions for generating a virtual representation of at least one datum associated with an angular-resolved and spectrally resolved dark-field image of the object one or more instructions for varying an illumination-collection spacing by varying at least one of an illumination angle of incidence or a collection aperture dimension based on a detected contrast differential one or more instructions for generating object identification information based on principal components information one or more instructions for generating object identification information based on discrimination filter information

Fig. 9

902 one or more instructions for acquiring a plurality of hyperspectral dark-field images of a biological object at a first field of view and a second field of view, for one or more dark-field apertures at each of the first field of view and the second field of view one or more instructions for classifying the biological object based on a comparison of an angular-resolved and spectrally resolved scattering matrix to reference angular-resolved and spectrally resolved information one or more instructions for generating an angular-resolved and spectrally resolved scattering matrix based on the plurality of hyperspectral dark-field images at the first field of view one or more instructions for generating an angular-resolved and spectrally resolved scattering matrix based on the plurality of hyperspectral dark-field images at the second field of view one or more instructions for generating an angular-resolved and spectrally resolved scattering matrix based on the plurality of hyperspectral dark-field images at the first field of view or the second field of view one or more instructions for generating hyperspectral information based on the plurality of hyperspectral dark-field images at the first field of view or the second field of view one or more instructions for classifying the biological object based on a comparison of the angular-resolved and spectrally resolved hyperspectral information to reference angular-resolved and spectrally resolved dark-filed information one or more instructions for generating registration information for real-time registering a biological object relative to a reference location

Fig. 10

1002 one or more instructions for generating an angular-resolved map for each of a plurality of pixels of a dark-field micrograph of at least a portion of an object under test one or more instructions for generating angular-resolved and spectrally resolved hyperspectral information based on a plurality of angular-resolved maps one or more instructions for classifying the biological sample based on a comparison of the angular-resolved and spectrally resolved hyperspectral information to reference angular-resolved and spectrally resolved information

Fig. 11

1102 one or more instructions for acquiring hyperspectral dark-field images or multispectral dark-field images, for at least a first field of view, and for at least a first dark-field aperture and a second dark-field aperture, the second dark-field aperture different from the first dark-field aperture one or more instructions for generating classification information associated with the object under test based on a comparison of the hyperspectral dark-field images or the multispectral dark-field images of the object to reference hyperspectral dark-field information or reference multispectral dark-field information

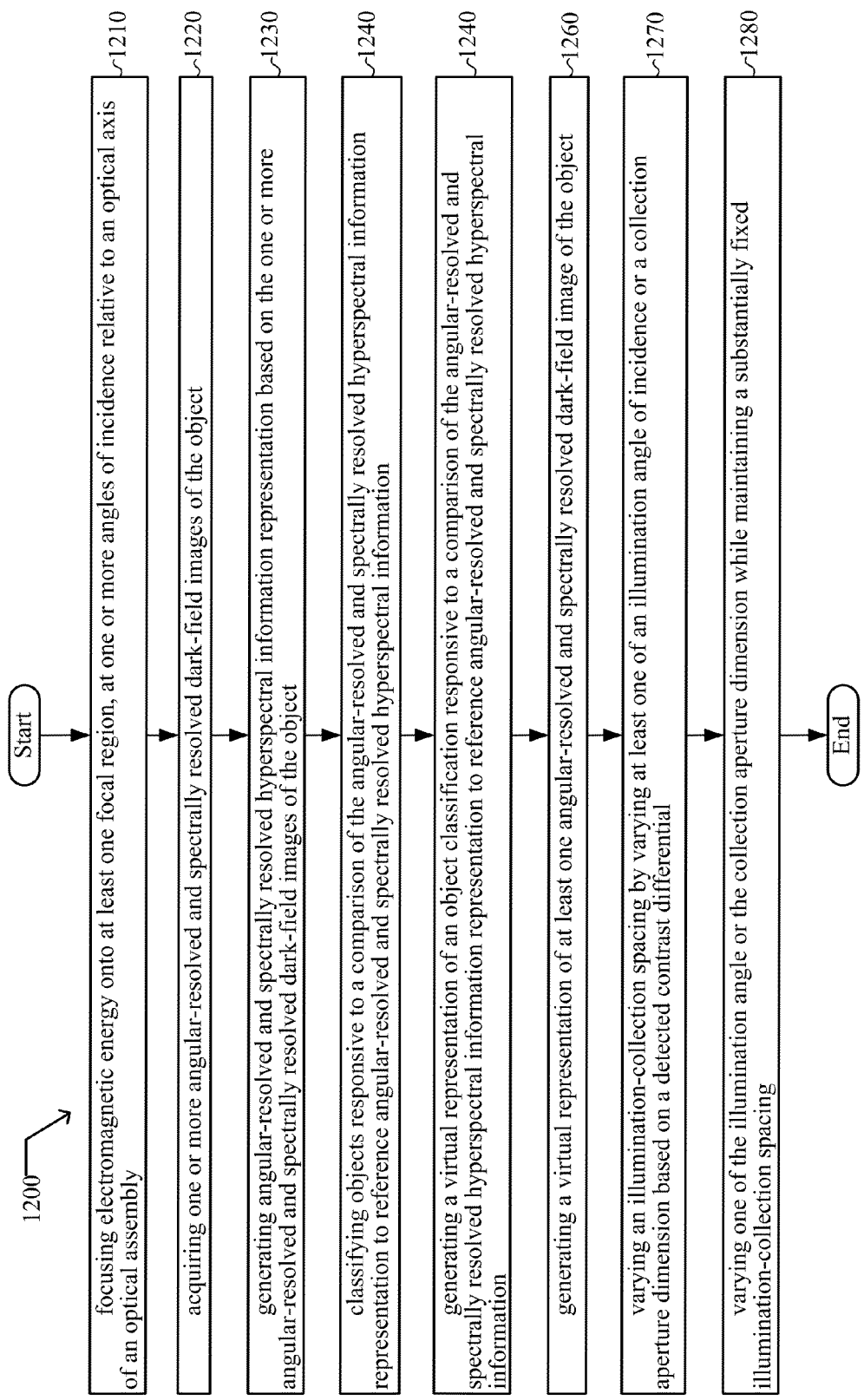

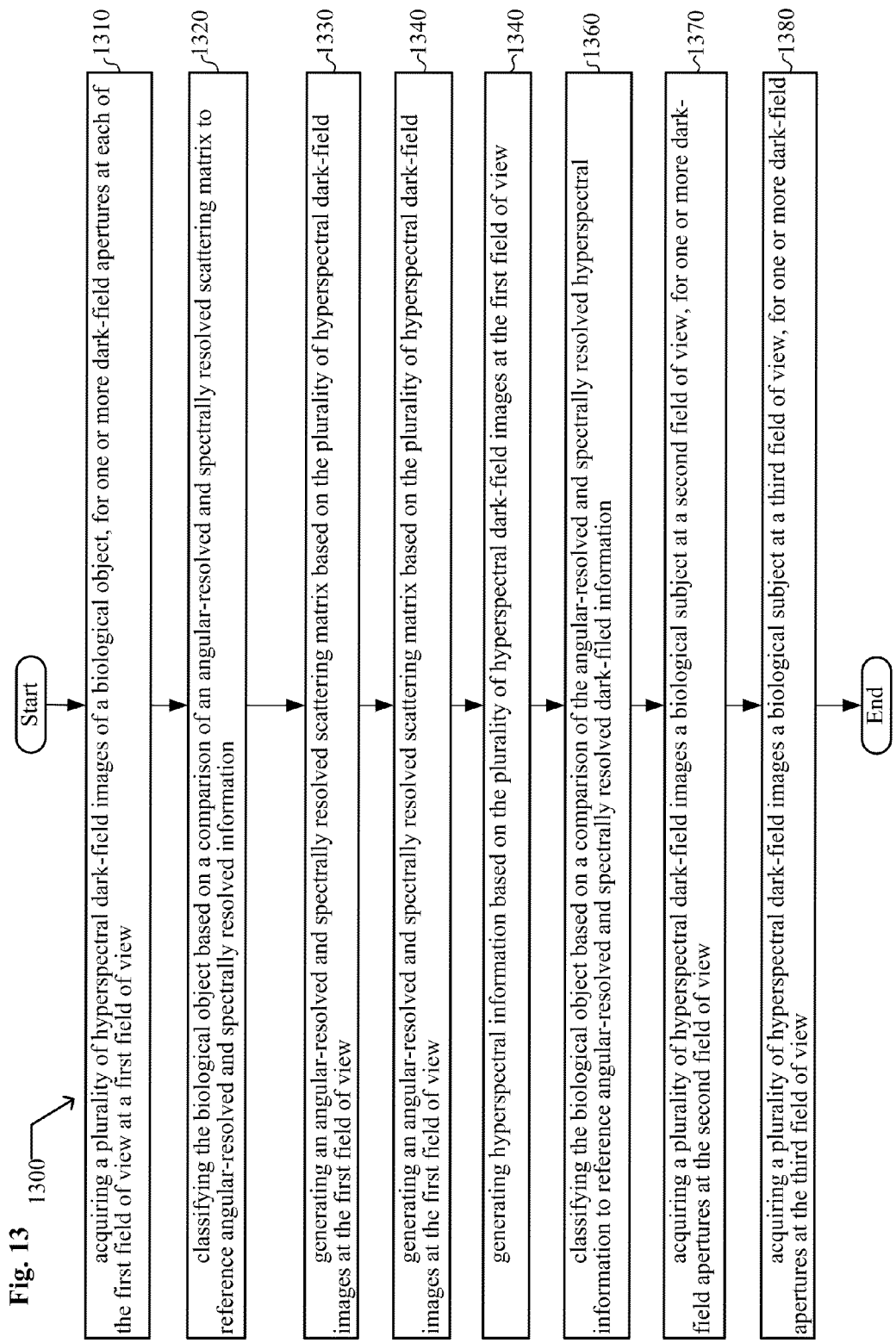

Fig. 14

1402 one or more instructions for acquiring a plurality of hyperspectral dark-field images a biological subject, for at least a first field of view and a second field of view, for one or more dark-field apertures at each of the first field of view and the second field of view one or more instructions for generating an angular-resolved and spectrally resolved hyperspectral dark-field information based on the plurality of hyperspectral dark-field images one or more instructions for classifying the biological object based on a comparison of the angular-resolved and spectrally resolved hyperspectral information to reference angular-resolved and spectrally resolved dark-filed information

SYSTEMS, DEVICES, AND METHODS EMPLOYING ANGULAR-RESOLVED SCATTERING AND SPECTRALLY RESOLVED MEASUREMENTS FOR CLASSIFICATION OF OBJECTS

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

None

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation (s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, the present disclosure is directed to, among other things, a hyperspectral imaging system. In an embodiment, the hyperspectral imaging system includes a dark-field module including an optical assembly, and a dark-field illuminator. In an embodiment, the dark-field module is operably coupled to one or more sensors and to the dark-field illuminator, and is configured to acquire one or more dark-field micrographs associated with scattered electromagnetic energy from an object interrogated by the dark-field interrogation stimulus. In an embodiment, the imaging system includes a dark-field illuminator configured to provide multi-angle illumination and to acquire wavelength and angle information for a plurality of pixels in a field of view. In an embodiment, the dark-field illuminator is operable to deliver a dark-field interrogation stimulus onto at least one focal region, at one or more angles of incidence relative to an optical axis of an optical assembly.

In an embodiment, the hyperspectral imaging system includes a hyperspectral imaging module operably coupled to the dark-field module and having circuitry configured to generate angular-resolved and spectrally resolved scattering information based on the one or more dark-field micrographs of an object. In an embodiment, the hyperspectral imaging system includes an object classification module having circuitry operable to compare the angular-resolved and spectrally resolved scattering information to reference angular-resolved and spectrally resolved hyperspectral information, and to generate classification information associated with objects imaged in the one or more dark-field micrographs based on the comparison.

In an aspect, the present disclosure is directed to, among other things, a hyperspectral imaging apparatus including a dark-field module and an object classification module. In an embodiment, the dark-field module is operably coupled to an optical assembly and is configured to focus electromagnetic energy onto at least one focal region, at one or more angles of incidence relative to an optical axis of the optical assembly. For example, in an embodiment, the dark-field module includes a plurality of energy emitters configured to focus electromagnetic energy, onto at least one focal region, at one or more angles of incidence relative to an optical axis of the optical assembly.

In an embodiment, the hyperspectral image sensor is operably coupled to the dark-field module. In an embodiment, the hyperspectral image sensor includes one or more electro-mechanical components, opto-mechanical components, electro-opto components, acousto-optic components, etc., configured to modulate an angle of incidence of electromagnetic energy delivered by the dark-field module, acquire one or more angular-resolved dark-field images of at least a portion of an object at different fields of view, and generate angular-resolved and spectrally resolved hyperspectral information based on one or more angular-resolved dark-field images. In an embodiment, the object classification module includes circuitry operable to compare the angular-resolved and spectrally resolved hyperspectral information to reference angular-resolved and spectrally resolved hyperspectral information, and to classify objects based on the comparison.

In an aspect, the present disclosure is directed to, among other things, a method for identifying, classifying, differentiating, etc., objects. In an embodiment, the method includes focusing electromagnetic energy onto at least one focal region, at one or more angles of incidence relative to an optical axis of an optical assembly. In an embodiment, the method includes acquiring one or more angular-resolved and spectrally resolved dark-field images of an object. In an embodiment, the method includes generating angular-resolved and spectrally resolved hyperspectral information representation based on the one or more angular-resolved and spectrally resolved dark-field images of an object. In an embodiment, the method includes classifying objects responsive to a comparison of the angular-resolved and spectrally resolved hyperspectral information representation to reference angular-resolved and spectrally resolved hyperspectral information.

In an embodiment, the method includes generating a virtual representation of an object classification responsive to a comparison of the angular-resolved and spectrally resolved hyperspectral information representation to reference angular-resolved and spectrally resolved hyperspectral information. In an embodiment, the method includes generating a virtual representation of at least one angular-resolved and spectrally resolved dark-field image of an object. In an embodiment, the method includes varying an illumination-collection spacing by varying at least one of an illumination angle of incidence or a collection aperture dimension based on a detected contrast differential. In an embodiment, the method includes varying one of the illumination angle or the collection aperture dimension while maintaining a substantially fixed illumination-collection spacing.

In an embodiment, the method includes determining significant objects information from a field of view using spatial image processing techniques such as T-test protocols, threshold test protocols, and the like. In an embodiment, the method includes determining scatter characteristics information of an object using one or more discriminating filters based on one or more of morphology information and scattering information.

In an aspect, the present disclosure is directed to, among other things, an article of manufacture including a non-transitory signal-bearing medium bearing one or more instructions for causing a system, computing device, processor, etc., to focus electromagnetic energy onto at least one focal region, at one or more angles of incidence relative to an optical axis of an optical assembly. In an embodiment, the article of manufacture includes a non-transitory signal-bearing medium bearing one or more instructions for causing a system, computing device, processor, etc., to acquire one or more angular-resolved and spectrally resolved dark-field images of an object. In an embodiment, the article of manufacture includes a non-transitory signal-bearing medium bearing one or more instructions for causing a system, computing device, microprocessor, etc., to generate angular-resolved and spectrally resolved hyperspectral information representation based on the one or more angular-resolved and spectrally resolved dark-field images of an object. In an embodiment, the article of manufacture includes a non-transitory signal-bearing medium bearing one or more instructions for causing a system, computing device, processor, etc., to classify objects in an object responsive to a comparison of the angular-resolved and spectrally resolved hyperspectral information representation to reference angular-resolved, and spectrally resolved hyperspectral information. In an embodiment, the article of manufacture includes a non-transitory signal-bearing medium bearing one or more instructions for causing a system, computing device, processor, etc., to generate a virtual representation of at least one datum associated with an angular-resolved, and spectrally resolved dark-field image of an object.

In an aspect, the present disclosure is directed to, among other things, a dark-field object classification apparatus. In an embodiment, the dark-field object classification apparatus includes an illumination-angle controller operable to modulate an angle of incidence of electromagnetic energy delivered by a dark-field illuminator, the dark-field illuminator oriented to focus electromagnetic energy onto at least one focal region, at one or more angles of incidence relative to an optical axis of an optical assembly. In an embodiment, the dark-field object classification apparatus includes an aperture controller operably coupled to an aperture device, the aperture controller operable to modulate an effective numerical aperture associated with a collection zone of scattered electromagnetic energy from an object interrogated by the electromagnetic energy delivered by the dark-field illuminator. In an embodiment, the dark-field object classification apparatus includes a hyperspectral image controller having circuitry configured to acquire one or more angular-resolved dark-field images of an object, generate an angular-resolved and spectrally resolved scattering matrix based on the one or more angular-resolved dark-field images, and generate object classification information based on the comparison.

In an aspect, the present disclosure is directed to, among other things, a hyperspectral image classification system. In an embodiment, the hyperspectral image classification system includes a dark-field illuminator operable to focus electromagnetic energy onto at least one focal region, at one or more angles of incidence relative to an optical axis of an optical assembly. In an embodiment, the hyperspectral image classification system includes a hyperspectral imaging module operably coupled to the dark-field illuminator and having sensors and circuitry configured to modulate an angle of incidence of electromagnetic energy delivered by the dark-field illuminator, modulate a controllable effective numerical aperture associated with a collection zone, acquire a spectrally resolved and angular-resolved map for a plurality of pixels of an image, and generate an angular-resolved and spectrally resolved scattering matrix based on the spectrally resolved and angular-resolved map for the plurality of pixels of an image. In an embodiment, the hyperspectral image classification system includes an object classification module operable to compare the angular-resolved and spectrally resolved scattering matrix to reference angular-resolved and spectrally resolved hyperspectral information, and to classify an object based on the comparison.

In an aspect, the present disclosure is directed to, among other things, a hyperspectral imaging system. In an embodiment, the hyperspectral imaging system includes a hyperspectral detection module having circuitry operably to acquire angular-resolved hyperspectral dark-field micrographs at one or more fields of view. In an embodiment, the hyperspectral imaging system includes an object classification module having circuitry operable to classify groups of pixels in the angular-resolved hyperspectral dark-field micrographs indicative of one or more imaged objects based on a comparison of the acquired angular-resolved hyperspectral information to reference angular-resolved and spectrally resolved hyperspectral information. In an embodiment, the object classification module includes circuitry operable to generate object morphological information based on the comparison.

In an aspect, the present disclosure is directed to, among other things, a hyperspectral imaging apparatus. In an embodiment, the hyperspectral imaging apparatus includes an optical assembly, a dark-field illuminator, and a collection aperture module. In an embodiment, the dark-field illuminator operable to focus electromagnetic energy onto at least one focal region, at one or more angles of incidence relative to an optical axis of the optical assembly. In an embodiment, the collection aperture module having circuitry operable to modulate an effective numerical aperture associated with a collection zone of scattered electromagnetic energy from an object interrogated by the electromagnetic energy delivered by the dark-field illuminator. In an embodiment, hyperspectral imaging apparatus includes a hyperspectral imaging module operably coupled to the dark-field illuminator and the collection aperture module, the hyperspectral imaging module having circuitry configured to modulate at least one of angle of incidence of electromagnetic energy delivered by the dark-field illuminator, or an effective numerical aperture associated with a collection zone, acquire a plurality of hyperspectral dark-field images of an object, at least at a first field of view, and generate an angular-resolved and spectrally resolved scattering matrix based on the plurality of hyperspectral dark-field images. In an embodiment, the hyperspectral imaging module further includes circuitry configured to compare angular-resolved and spectrally resolved scattering matrix information to reference angular-resolved and spectrally resolved hyperspectral information, and classify an object based on the comparison.

In an aspect, the present disclosure is directed to, among other things, an object classification apparatus. In an embodiment, the object classification apparatus includes an object tracking module including circuitry configured to track an object in a field of view of a dark-field imager. In an embodiment, the object classification apparatus includes a dark-field illuminator operably coupled to the object tracking module and configured to deliver a dark-field interrogation stimulus onto at least one focal region in the field of view of the dark-field imager, at one or more angles of incidence relative to an optical axis of an optical assembly. In an embodiment, the object classification apparatus includes an object identification module including circuitry configured to identify a property of an object within the field of view of the dark-field imager using at least one datum associated with an angular-resolved and spectrally resolved scattering matrix of an object.

In an aspect, the present disclosure is directed to, among other things, an article of manufacture including a non-transitory signal-bearing medium bearing one or more instructions for causing a system, computing device, processor, etc., to acquire a plurality of hyperspectral dark-field images of a biological object at a first field of view and a second field of view, for one or more dark-field apertures, at each of the first field of view and the second field of view.

In an embodiment, the article of manufacture includes a non-transitory signal-bearing medium bearing one or more instructions for causing a system, computing device, processor, etc., to classify the biological object based on a comparison of an angular-resolved and spectrally resolved scattering matrix to reference angular-resolved, and spectrally resolved information. In an embodiment, the article of manufacture includes a non-transitory signal-bearing medium bearing one or more instructions for causing a system, computing device, processor, etc., to generate an angular-resolved and spectrally resolved scattering matrix based on the plurality of hyperspectral dark-field images at the first field of view.

In an embodiment, the article of manufacture includes a non-transitory signal-bearing medium bearing one or more instructions for causing a system, computing device, processor, etc., to generate an angular-resolved and spectrally resolved scattering matrix based on the plurality of hyperspectral dark-field images at the second field of view. In an embodiment, the article of manufacture includes a non-transitory signal-bearing medium bearing one or more instructions for causing a system, computing device, processor, etc., to generate an angular-resolved and spectrally resolved scattering matrix based on the plurality of hyperspectral dark-field images at the first field of view or the second field of view.

In an embodiment, the article of manufacture includes a non-transitory signal-bearing medium bearing one or more instructions for causing a system, computing device, processor, etc., to generate hyperspectral information based on the plurality of hyperspectral dark-field images at the first field of view or the second field of view. In an embodiment, the article of manufacture includes a non-transitory signal-bearing medium bearing one or more instructions for causing a system, computing device, processor, etc., to classify the biological object based on a comparison of the angular-resolved and spectrally resolved hyperspectral information to reference angular-resolved, and spectrally resolved dark-field information.

In an embodiment, the article of manufacture includes a non-transitory signal-bearing medium bearing one or more instructions for causing a system, computing device, processor, etc., to generate registration information for real-time registering a biological object relative to a reference location. In an aspect, the present disclosure is directed to, among other things, method including acquiring a plurality of hyperspectral dark-field images of a biological object, for one or more dark-field apertures at each of the first field of view at a first field of view. In an embodiment, the method includes classifying the biological object based on a comparison of an angular-resolved and spectrally resolved scattering matrix to reference angular-resolved and spectrally resolved information. In an embodiment, the method includes generating an angular-resolved and spectrally resolved scattering matrix based on the plurality of hyperspectral dark-field images at the first field of view. In an embodiment, the method includes generating an angular-resolved and spectrally resolved scattering matrix based on the plurality of hyperspectral dark-field images at the first field of view.

In an embodiment, the method includes generating hyperspectral information based on the plurality of hyperspectral dark-field images at the first field of view, and classifying the biological object based on a comparison of the angular-resolved and spectrally resolved hyperspectral information to reference angular-resolved and spectrally resolved dark-field information. In an embodiment, the method includes acquiring a plurality of hyperspectral dark-field images of a biological subject at a second field of view, for one or more dark-field apertures at the second field of view. In an embodiment, the method includes acquiring a plurality of hyperspectral dark-field images of a biological subject at a third field of view, for one or more dark-field apertures at the third field of view.

In an aspect, the present disclosure is directed to, among other things, an object classification apparatus including a resolution modification module having circuitry configured to modify a pixel count of at least one micrograph and to generate at least a first modified micrograph. In an embodiment, the object classification apparatus includes a scattering filter module having circuitry operable to isolate a scattering array for at least one of the objects imaged in the first modified micrograph. In an embodiment, the object classification apparatus includes an object identification module having circuitry operable to analyze principal components of the isolated scattering array, and to classify the at least one of the objects imaged in the first modified micrograph based on one or more linear discrimination filters.

In an aspect, the present disclosure is directed to, among other things, an article of manufacture including a non-transitory signal-bearing medium bearing one or more instructions for causing a system, computing device, processor, etc., to acquire a plurality of hyperspectral dark-field images of an object, for at least a first field of view and a second field of view, for one or more dark-field apertures, at each field of view. In an embodiment, the article of manufacture includes a non-transitory signal-bearing medium bearing one or more instructions for causing a system, computing device, processor, etc., to generate an angular-resolved and spectrally resolved hyperspectral dark-field information based on the plurality of hyperspectral dark-field images. In an embodiment, the article of manufacture includes a non-transitory signal-bearing medium bearing one or more instructions for causing a system, computing device, processor, etc., to classify an object based on a comparison of the angular-resolved and spectrally resolved hyperspectral information to reference angular-resolved, and spectrally resolved dark-field information.

In an aspect, the present disclosure is directed to, among other things, an article of manufacture including a non-transitory signal-bearing medium bearing one or more instructions for causing a system, computing device, processor, etc., to generate an angular-resolved map for each of a plurality of pixels of a dark-field micrograph of at least a portion of an object under test. In an embodiment, the article of manufacture includes a non-transitory signal-bearing medium bearing one or more instructions for causing a system, computing device, processor, etc., to generate angular-resolved and spectrally resolved hyperspectral information based on a plurality of angular-resolved maps. In an embodiment, the article of manufacture includes a non-transitory signal-bearing medium bearing one or more instructions for causing a system, computing device, processor, etc., to classify the biological sample based on a comparison of the angular-resolved and spectrally resolved hyperspectral information to reference angular-resolved, and spectrally resolved information.

In an aspect, the present disclosure is directed to, among other things, an article of manufacture including a non-transitory signal-bearing medium bearing one or more instructions for causing a system, computing device, processor, etc., to acquire hyperspectral dark-field images or multispectral dark-field images, for at least a first field of view, and for at least a first dark-field aperture and a second dark-field aperture, the second dark-field aperture different from the first dark-field aperture. In an embodiment, the article of manufacture includes a non-transitory signal-bearing medium bearing one or more instructions for causing a system, computing device, processor, etc., to generate classification information associated with an object under test based on a comparison of the hyperspectral dark-field images or the multispectral dark-field images of an object to reference hyperspectral dark-field information or reference multispectral dark-field information.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 8 shows a schematic diagram of an article of manufacture according to one embodiment.

FIG. 9 shows a schematic diagram of an article of manufacture according to one embodiment.

FIG. 10 shows a schematic diagram of an article of manufacture according to one embodiment.

FIG. 11 shows a schematic diagram of an article of manufacture according to one embodiment.

FIG. 12 is a flow diagram of a method according to one embodiment.

FIG. 13 is a flow diagram of a method according to one embodiment.

FIG. 14 is a flow diagram of a method according to one embodiment.

DETAILED DESCRIPTION

Figure 1:
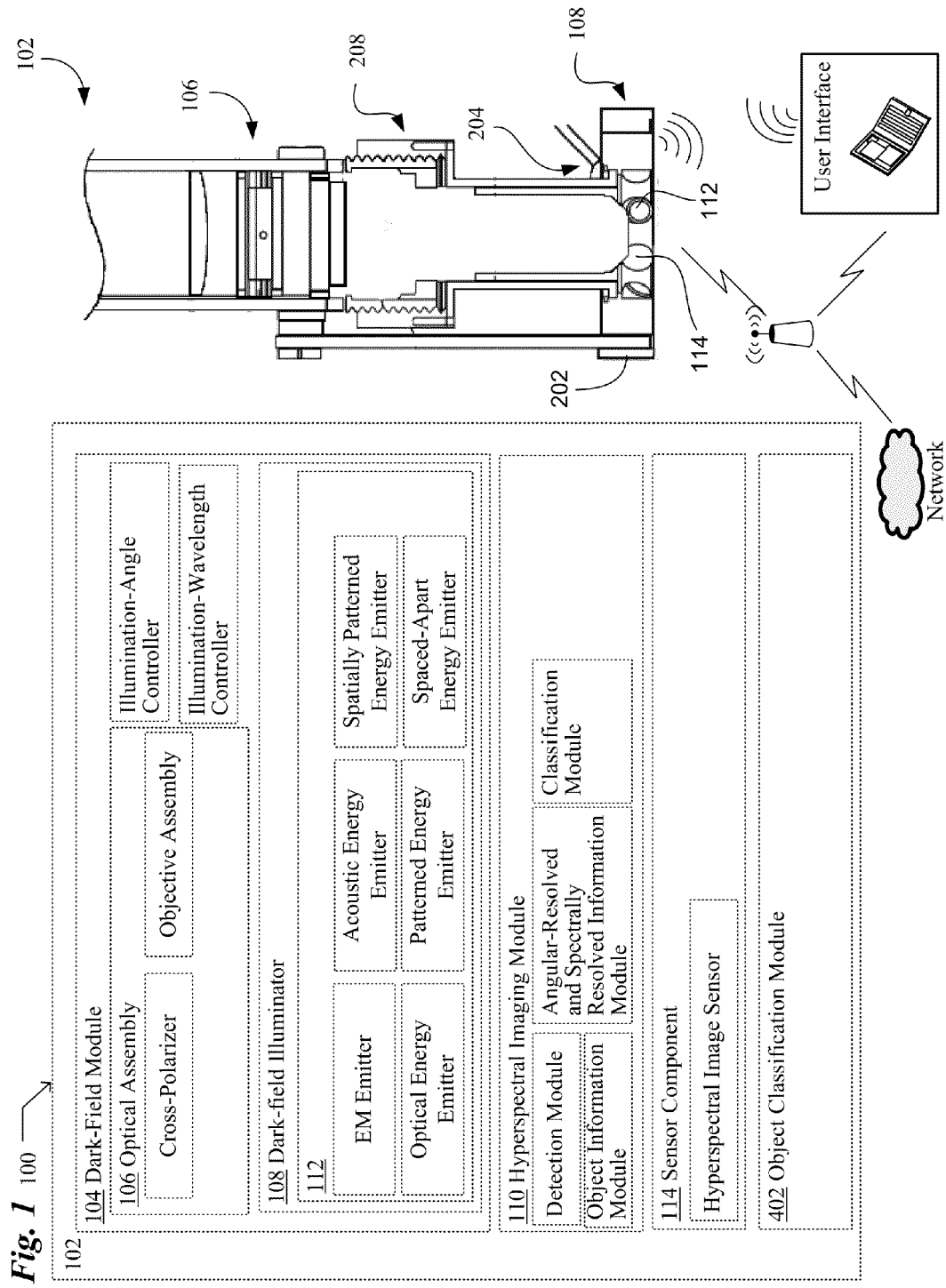
FIG. 1 is a perspective view of an identification, classification, differentiation, etc., system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In an embodiment, dark-field, angle-resolved multispectral imaging, systems, devices, and methods provide identification, classification, differentiation, etc., of objects (e.g., particles, biological samples, bacteria, cell membrane structures, etc.). In an embodiment, systems, devices, and methods provide identification, classification, differentiation, etc., of objects such as for example, cells, whole-organisms, bacteria, contaminates, parasites, and the like. In an embodiment, systems, devices, and methods provide identification, classification, differentiation, etc., of objects found in, for example, food composition, aqueous mixtures, soil admixtures, and the like.

In an embodiment, systems, devices, and methods are provided for identifying, classifying, differentiating, etc., objects utilizing all-optical approaches without the need for stains, chemicals, or culturing protocols. In an embodiment, dark-field systems, dark-field devices, and dark-field methods are provided for identifying, classifying, differentiating, etc., objects based on at least one datum derived from angular-resolved and spectrally resolved scattering micrographs of an object. In an embodiment, systems, devices, and methods are provided for interrogating objects, and for generating dark-field, multispectral, scattering angle, information, and for identifying, classifying, differentiating, etc., interrogated objects (e.g., particles, biological samples, bacteria, cell membrane structures, etc.)

Figure 2:
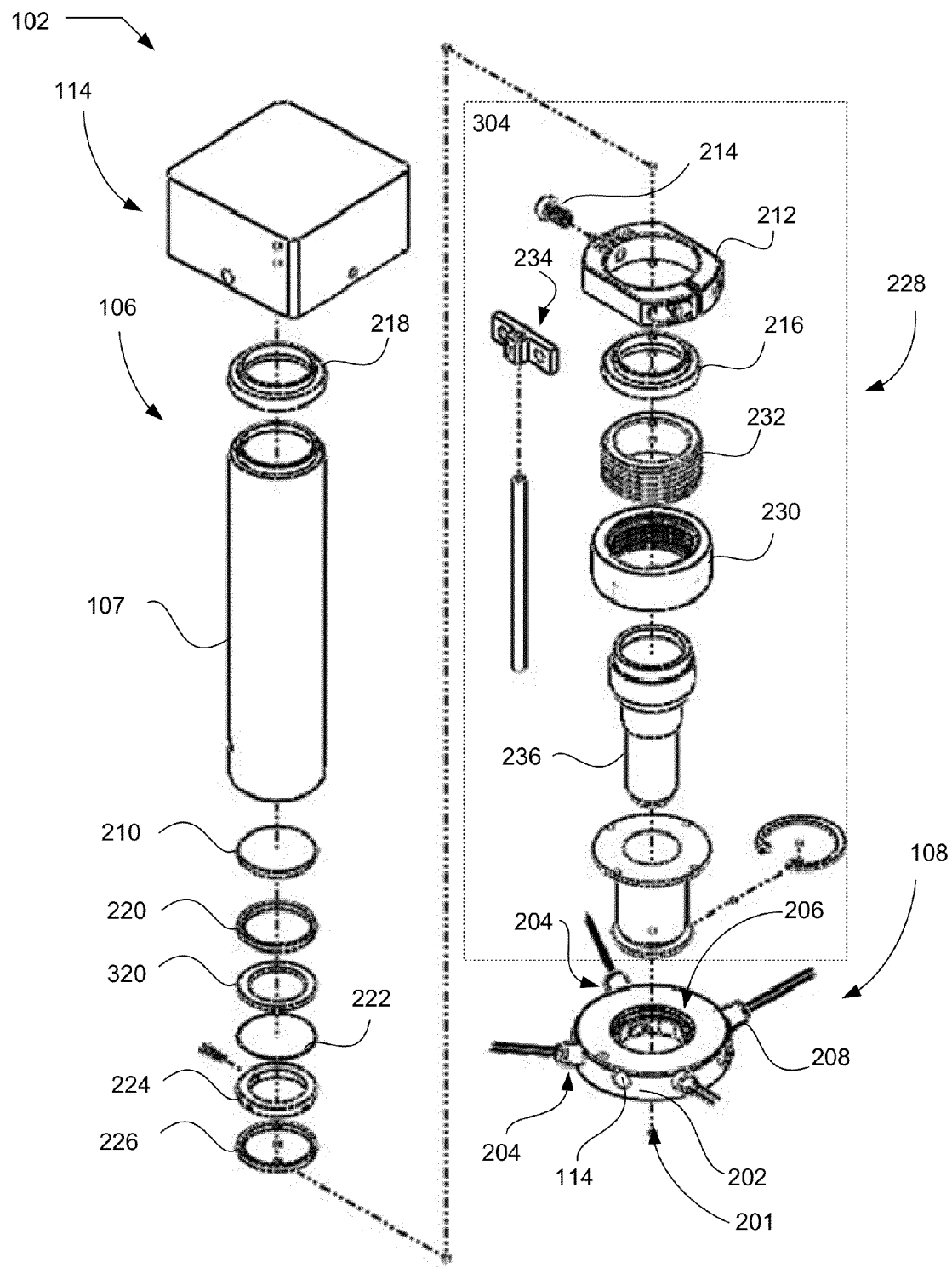
FIG. 2 is a perspective view of an identification, classification, differentiation, etc., system according to one embodiment.
Figure 3:
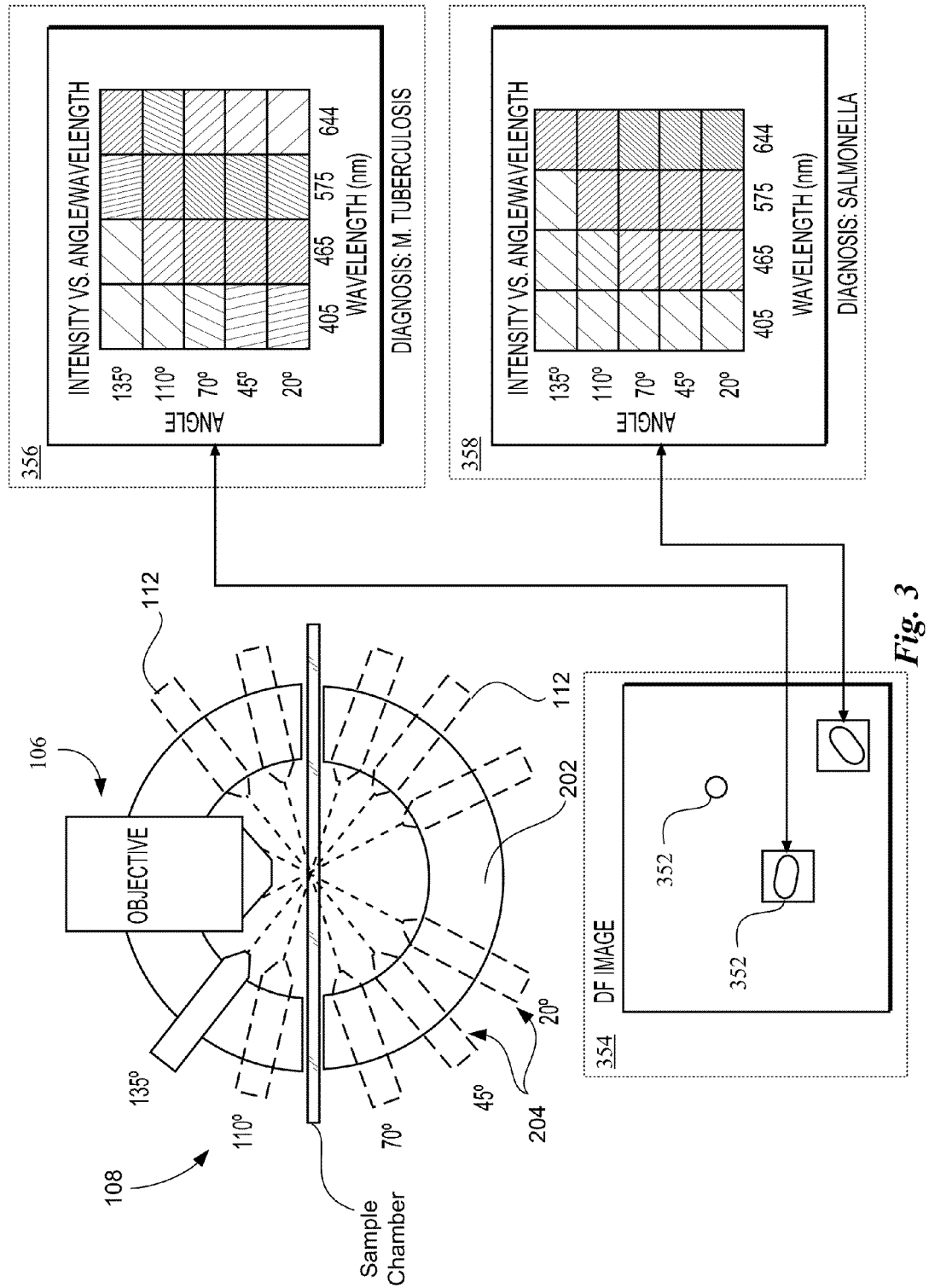
FIG. 3 is a perspective view of an identification, classification, differentiation, etc., system according to one embodiment.

FIGS. 1-3 shows a system 100 (e.g., a classification system, a differentiation system, an identification system, an imaging system, an object classification system, an object differentiation system, an object identification system, an object monitoring system a hyperspectral imaging system, a multi-angle dark-field imaging system, and the like) in which one or more methodologies or technologies can be implemented, such as for example, identifying, classifying, differentiating, etc., objects (e.g., cells, bacteria, bacterial diseases, contaminants, and the like). In an embodiment, the system 100 includes one or more apparatus 102 (e.g., imagers, classifiers, differentiators, identifiers, classification apparatus, differentiation apparatus, identification apparatus, hyperspectral imaging apparatus, etc.) (See, e.g., U.S. Patent Publication No. 2011/0222059 (published Sep. 15, 2011); which is incorporated herein by reference). In an embodiment, the system 100 includes a dark-field module 104. In an embodiment, the dark-field module 104 is operably coupled to an optical assembly 106 and a dark-field illuminator 108, and is configured to acquire one or more dark-field micrographs associated with scattered electromagnetic energy from an object interrogated by a dark-field interrogation stimulus. In an embodiment, the system 100 includes a hyperspectral imaging module 110. In an embodiment, the hyperspectral imaging module 110 is operably coupled to at least one of the dark-field module 104 and the hyperspectral imaging module 110, and is configured to generate an angular-resolved and spectrally resolved scattering matrix based on the one or more dark-field micrographs of an object.

In an embodiment, a module includes, among other things, one or more computing devices such as a processor (e.g., a microprocessor), a central processing unit (CPU), a digital signal processor (DSP), an application-specific integrated circuit (ASIC), a field programmable gate array (FPGA), and the like, or any combinations thereof, and can include discrete digital or analog circuit elements or electronics, or combinations thereof. In an embodiment, a module includes one or more ASICs having a plurality of predefined logic components. In an embodiment, a module includes one or more FPGAs, each having a plurality of programmable logic components.

In an embodiment, a module includes circuitry having one or more components operably coupled (e.g., communicatively, electromagnetically, magnetically, ultrasonically, optically, inductively, electrically, capacitively coupled, and the like) to each other. In an embodiment, a module includes one or more remotely located components. In an embodiment, remotely located components are operably coupled, for example, via wireless communication. In an embodiment, remotely located components are operably coupled, for example, via one or more receivers, transmitters, transceivers, and the like. In an embodiment, the dark-field module 104 is operably coupled to a module having one or more routines, components, data structures, interfaces, and the like.

In an embodiment, a module includes memory that, for example, stores instructions or information. For example, in an embodiment, at least one control module includes memory that stores object identification information, object classification information, and object characterization information, and the like. Non-limiting examples of memory include volatile memory (e.g., Random Access Memory (RAM), Dynamic Random Access Memory (DRAM), and the like), non-volatile memory (e.g., Read-Only Memory (ROM), Electrically Erasable Programmable Read-Only Memory (EEPROM), Compact Disc Read-Only Memory (CD-ROM), and the like), persistent memory, and the like. Further non-limiting examples of memory include Erasable Programmable Read-Only Memory (EPROM), flash memory, and the like. In an embodiment, the memory is coupled to, for example, one or more computing devices by one or more instructions, information, or power buses. For example, in an embodiment, the dark-field module 104 includes memory that, for example, stores object identification information, object classification information, object characterization information, and the like.

In an embodiment, a module includes one or more computer-readable media drives, interface sockets, Universal Serial Bus (USB) ports, memory card slots, and the like, and one or more input/output components such as, for example, a graphical user interface, a display, a keyboard, a keypad, a trackball, a joystick, a touch-screen, a mouse, a switch, a dial, and the like, and any other peripheral device. In an embodiment, a module includes one or more user input/output components that are operably coupled to at least one computing device configured to control (electrical, electromechanical, software-implemented, firmware-implemented, or other control, or combinations thereof) at least one parameter associated with, for example, modulating an effective numerical aperture associated with a collection zone of scattered electromagnetic energy from an object interrogated by the dark-field interrogation stimulus.

In an embodiment, a module includes a computer-readable media drive or memory slot that is configured to accept signal-bearing medium (e.g., computer-readable memory media, computer-readable recording media, and the like). In an embodiment, a program for causing a system to execute any of the disclosed methods can be stored on, for example, a computer-readable recording medium (CRMM), a signal-bearing medium, and the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, and the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.).) Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINI-DISC, non-volatile memory card, EEPROM, optical disk, optical storage, RAM, ROM, system memory, web server, and the like.

In an embodiment, the dark-field module 104 includes a plurality of energy-emitting components 112 configured to interrogate one or more focal volumes with an electromagnetic energy stimulus. Non-limiting examples of energy-emitting components 112 include electromagnetic radiation emitters, electric circuits, electrical conductors, cavity resonators, electro-mechanical components, electro-opto components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency light-emitting diodes, and the like), arc flashlamps, incandescent emitters, continuous wave bulbs, and the like. In an embodiment, the energy-emitting component 112 includes at least one two-photon excitation component. In an embodiment, the energy-emitting component 112 includes one or more lasers, laser diodes, light-emitting diodes, and the like. In an embodiment, the energy-emitting component 112 includes one or more quantum dots, organic light-emitting diodes, microcavity light-emitting diodes, polymer light-emitting diodes, and the like. In an embodiment, the energy-emitting component 112 includes at least one of an exciplex laser, a diode-pumped solid-state laser, or a semiconductor laser. In an embodiment, the energy-emitting component 112 includes one or more tunable ultrafast lasers. In an embodiment, the energy-emitting component 112 includes one or more femtosecond lasers. In an embodiment, the energy-emitting component 112 includes one or more Ti:sapphire lasers. In an embodiment, the energy-emitting component 112 interrogates at least one focal volume with a spatially patterned electromagnetic energy stimulus having at least a first region and a second region different from the first region. In an embodiment, the energy-emitting component 112 interrogates at least one focal volume with a spatially-patterned electromagnetic energy stimulus having at least a first region and a second region, the second region having at least one of an illumination intensity, an energy-emitting pattern, a peak emission wavelength, an ON-pulse duration, an OFF-pulse duration, or a pulse frequency different from the first region. In an embodiment, the energy-emitting component 112 interrogates at least one focal volume with a spatially patterned pulsed multiplexed electromagnetic energy stimulus. In an embodiment, the energy-emitting component 112 generates a multiplexed electromagnetic energy stimulus having, for example, two or more peak emission wavelengths.

In an embodiment, the dark-field module 104 is operably coupled to at least one of a Bayer filter camera, a hyperspectral camera (e.g., scanning slit based, multi array based, and the like), a monochromator, a multiple narrow band light, and multiple narrow band light. For example, in an embodiment, the dark-field module 104 is operably coupled to a Bayer filter camera. In an embodiment, the dark-field module 104 is operably coupled to a hyperspectral camera (e.g., scanning slit based, multi array based, and the like). In an embodiment, the dark-field module 104 is operably coupled to a monochromator and a white light illuminator. In an embodiment, the dark-field module 104 is operably coupled to multiple narrow band light sources as substitution in a white illumination configuration. In an embodiment, the dark-field module 104 is operably coupled to a multiple narrow band light sources and a dark-field illuminator 108.

In an embodiment, the dark-field module 104 includes an energy-emitting component 112 configured to direct (e.g., via one or more waveguides) electromagnetic radiation toward a sample including one or more objects. In an embodiment, by adjusting the wavelength of the electromagnetic stimulus generated by the energy emitting component 104, it is possible to control the wavelength of light that emerges from a sample having non-linear properties (i.e., it is possible to control the wavelength of the emerging nonlinear optical response of the sample.) In an embodiment, one or more peak emission wavelengths of the electromagnetic stimulus generated by the energy-emitting component 112 are chosen to elicit a nonlinear optical response of the sample to emit within a wavelength range that damages genetic material.

In an embodiment, the dark-field module 104 includes an energy-emitting component 112 configured to deliver a spatially patterned pulsed multiplexed electromagnetic energy stimulus having a peak power ranging from about 400 gigawatts to about 8 terawatts. In an embodiment, the energy-emitting component 112 generates a spatially-patterned pulsed multiplexed electromagnetic energy stimulus having a peak irradiance of less than about 200 gigawatts/cm^2. In an embodiment, the energy-emitting component 112 generates a pulsed, spatially-patterned, multiplexed electromagnetic energy stimulus having an average power ranging from about 1 milliwatt to about 1 watt. In an embodiment, the energy-emitting component 112 generates a spatially-patterned pulsed multiplexed electromagnetic energy stimulus having one or more peak emission wavelengths ranging from about 690 nanometers to about 2000 nanometers. In an embodiment, the energy-emitting component 112 generates spatially-patterned pulsed multiplexed electromagnetic energy stimulus having a resolution [0.61*(peak emission wavelength/numerical aperture)] ranging from about 300 nanometers to about 10 micrometers. Energy-emitting components 112 forming part of an apparatus 102, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, and the like, or any combination thereof. One or more of the energy-emitting components 112 may have a peak emission wavelength in the x-ray, ultraviolet, visible, infrared, near infrared, terahertz, microwave, or radio frequency spectrum. In an embodiment, the energy-emitting component 112 includes a patterned energy-emitting source. In an embodiment, the energy-emitting component 112 includes a patterned light-emitting source.

In an embodiment, the dark-field module 104 includes an energy-emitting component 112 configured to concurrently or sequentially interrogate multiple focal volumes with the spatially-patterned pulsed multiplexed electromagnetic energy stimulus. In an embodiment, the energy-emitting component 112 concurrently or sequentially interrogates multiple focal volumes with a spatially-patterned, multifocal depth, electromagnetic energy stimulus.

In an embodiment, the dark-field module 104 includes an energy-emitting component 112 configured to deliver an electromagnetic energy stimulus having at least a first peak emission wavelength and a second peak emission wavelength different from the first peak emission wavelength. In an embodiment, the energy-emitting component 112 includes at least one of a first energy emitter and at least one of a second energy emitter, the at least one second energy emitter having a peak emission wavelength different from the at least one first energy emitter. In an embodiment, the energy-emitting component 112 concurrently or sequentially delivers a first pulsed electromagnetic energy stimulus and a second pulse electromagnetic energy stimulus, the second pulsed energy stimulus having at least one of a pulse duration, a pulse frequency, a pulse intensity, a pulse ratio, or a pulse repetition rate different from the first pulsed electromagnetic energy stimulus. In an embodiment, the energy-emitting component 112 concurrently or sequentially delivers a first pulsed electromagnetic energy stimulus and a second pulse electromagnetic energy stimulus, the second pulsed electromagnetic energy stimulus having a focal depth different from the first pulsed electromagnetic energy stimulus. In an embodiment, the energy-emitting component 112 concurrently or sequentially delivers a first pulsed electromagnetic energy stimulus and a second pulse electromagnetic energy stimulus, the second pulsed electromagnetic energy stimulus having a resolution different from the first pulsed electromagnetic energy stimulus.

In an embodiment, the dark-field module 104 includes an energy-emitting component 112 configured to deliver a spatially-focused electromagnetic energy stimulus onto a focal volume. In an embodiment, the energy-emitting component 112 includes a lens array configured to deliver spaced-apart energy stimuli having at least a first region and at least a second region, the second region having a focal depth different from the first region. In an embodiment, the second region has a peak emission wavelength different from the first region. In an embodiment, the second region has a peak irradiance different from the first region. In an embodiment, the second region has at least one of an intensity, frequency, pulse intensity, pulse duration, pulse ratio, and pulse repetition rate different from an intensity, frequency, pulse intensity, pulse duration, pulse ratio, and pulse repetition rate of the first region. In an embodiment, the energy-emitting components 112 are operably coupled to one or more orthogonal (or crossed) polarizers. In an embodiment, the dark-field module 104 is operably coupled to a sensor component 114 including one or more orthogonal (or crossed) polarizers.

In an embodiment, the energy-emitting component 112 includes a plurality of selectively-actuatable electromagnetic energy waveguides that direct an emitted spatially-patterned pulsed multiplexed electromagnetic energy stimulus to one or more regions of the at least one focal volume. In an embodiment, the energy-emitting component 112 includes a dark-field electromagnetic energy emitting component to deliver a multi-mode dark-field interrogation stimulus to at least one blood vessel.

In an embodiment, the dark-field module 104 includes circuitry operably coupled to one or more sensors and configured to acquire one or more dark-field micrographs associated with scattered electromagnetic energy from an object interrogated by a dark-field interrogation stimulus. In an embodiment, the dark-field module 104 includes circuitry operably to control an angle of incidence of electromagnetic energy delivered by a dark-field illuminator 108. For example, in an embodiment, the dark-field module 104 includes circuitry operably coupled to one or more waveguide assemblies of the dark-field illuminator 108. In an embodiment, the one or more waveguide assemblies are configured to change an angle of incidence of electromagnetic energy delivered by the dark-field illuminator 108 in response to an applied current.

In an embodiment, the dark-field module 104 includes at least one of an electro-mechanical component, an opto-mechanical component, an electro-optic component, or an acousto-optic component. In an embodiment, the electro-mechanical component, the opto-mechanical component, the electro-optic component, or the acousto-optic component is configured to change an angle of incidence of electromagnetic energy delivered by the dark-field illuminator 108 when activated. For example, in an embodiment, the dark-field module 104 includes circuitry operably coupled to an optical waveguide configured to change an angle of incidence of electromagnetic energy delivered by one or more of a plurality of waveguide assemblies forming part of the dark-field illuminator 108. In an embodiment, the system 100 includes a dark-field module 104 configured to provide multi-angle illumination and to acquire wavelength and angle information for every pixel in a field of view. In an embodiment, the dark-field module 104 is operably coupled to one or more modules including circuitry for generating an angle-resolved multispectral image. In an embodiment, the dark-field module 104 is operably coupled to one or more modules including circuitry for generating an angular-resolved and spectrally resolved scattering matrix based on the one or more dark-field micrographs of an object.

Referring to FIG. 3, in an embodiment, the dark-field module 104 is operably coupled to a multi-angle dark-field illuminator 108 that is configured to acquire wavelength and angle information for a plurality of pixels in a field of view associated with objects 352 imaged in the one or more dark-field images 354 based on the comparison. In embodiment, such configuration is operably for generating angle-resolved multispectral information resulting in dark-field images 354 where multispectral and scattering angle information (e.g., a scattering matrix, a scattering matrix map, etc.) can be extracted from any defined area of the dark-field image 354. For example, in an embodiment, the hyperspectral imaging module 110 includes circuitry configured to generate pixel by pixel, wavelength versus illumination angle intensity maps 356, 358 for an object 352 interrogated by a dark-field interrogation stimulus.

Referring to FIGS. 1-4, in an embodiment, the system 100 includes an optical assembly 106. In an embodiment, the optical assembly 106 can take a variety of forms and configurations. In an embodiment, the optical assembly 106 includes one or more lenses, optical elements (e.g., a beamsplitter, lens, gratings, etc.) diffractive elements (e.g., diffractive optical elements, aspheric diffractive lenses, diffusers, Fresnel lenses, etc.), filters, polarizers, and the like to guide, shape, vary, control, etc., electromagnetic radiation from a source (e.g., an energy-emitting component 112, and the like). Non-limiting examples of lenses include cylindrical graded index (GRIN) lenses, doublet or triplet lenses, that gather and shape electromagnetic radiation from a source (e.g., an energy-emitting component 112, a nonlinear optical response, and the like). Where the electromagnetic radiation source includes optical fibers that feed one or more lenses, the lenses are optionally bonded to or integral with the fibers.

In an embodiment, the optical assembly 106 includes one or more of polarization sensitive materials, chromatic correction, or other optical techniques for controlling the shape, phase, polarization, or other characteristics of the electromagnetic radiation. In an embodiment, dark-field illumination detection techniques can be further enhanced in contrast, selectivity, etc., by adding polarizers (e.g., orthogonal polarizers, crossed polarizers, and the like) to the by the dark-field illuminator 108 and a detector component 114. In an embodiment, cross polarization limits detection to scattering events that depolarize the illumination, greatly reducing false positives and unwanted signal. In an embodiment, the optical assembly 106 is operably coupled to one or more polarizers, color filters, exit pupil expanders, chromatic correction elements, eye-tracking elements, background mask, and the like. In an embodiment, the optical assembly 106 includes at least one Rheinberg filter. In an embodiment, the optical assembly 106 includes an objective assembly 106 having a selectively controllable numerical aperture ranging from about 0.5 to about 1.4. In an embodiment, the objective assembly 106 is configured to detect the nonlinear multi-harmonic response energy includes a computing device for actively controlling a numerical aperture of an objective assembly 106 having a selectively controllable numerical aperture ranging from about 0.5 to about 1.4. In an embodiment, the system 100 includes an objective assembly 106 having a numerical aperture ranging from about 0.5 to about 1.4. In an embodiment, the optical assembly 106 receives a portion of scattered radiation in a dark-field collection configuration. In an embodiment, the optical assembly 106 receives a portion of scattered radiation in a Rheinberg collection configuration. In an embodiment, the optical assembly 106 receives a portion of scattered radiation in an epi-collection configuration.

FIG. 2 shows an apparatus 102, in which one or more methodologies or technologies can be implemented such as, for example, detecting, classifying, identifying, etc., objects in a sample. In an embodiment, the apparatus 102 is configured to detect (e.g., assess, calculate, evaluate, determine, gauge, identify, measure, monitor, quantify, resolve, sense, or the like) an object present in, for example, a biological sample (e.g., blood, bone, muscle, skin, adipose tissue, fluid, tendons, organs, ventricles, or the like, either in vivo or in vitro). In an embodiment, the apparatus 102 includes a dark-field illuminator 108. In an embodiment, the apparatus 102 includes an optical assembly 106. In an embodiment, the apparatus 102 includes a sensor component 114. In an embodiment, the apparatus 102 includes an optical assembly 106 having a sample side, a detector side, and an optical axis 201 therethrough; and a dark-field illuminator 108 proximate the sample side of the optical assembly 106.

In an embodiment, the dark-field illuminator 108 includes a body structure 202 having a plurality of waveguide assemblies 204 and a sensor component 114 including one or more sensors configured to receive scattered electromagnetic energy from a sample interrogated by the dark-field illuminator 108. In an embodiment, the plurality of waveguide assemblies 204 includes at least a first electromagnetic energy emitter and a second electromagnetic energy emitter, the second electromagnetic energy emitter having at least one of an illumination intensity, a peak emission wavelength, or a pulse frequency different from the first electromagnetic energy emitter. In an embodiment, the sensor component 114 includes a sensor array for acquiring angle-dependent electromagnetic energy scattering information. In an embodiment, the sensor component 114 includes a sensor array for acquiring wavelength-dependent electromagnetic energy scattering information.

In an embodiment, the dark-field illuminator 108 includes a plurality of waveguide assemblies 204 and a body structure 202 having an aperture 206. In an embodiment, the dark-field illuminator 108 is configured to deliver electromagnetic energy through a plurality of waveguide assemblies 204 onto at least one focal region at one or more angles of incidence relative to an optical axis of an optical assembly 106. For example, in an embodiment, the plurality of waveguide assemblies 204 are oriented to focus electromagnetic energy onto at least one focal region, at one or more angles of incidence relative to an optical axis of an optical assembly 106. In an embodiment, the dark-field illuminator 108 is configured to rotate about an axis substantially parallel to the optical axis. In an embodiment, the dark-field illuminator 108 is configured to deliver a plurality of electromagnetic energy beams onto a focal region at two or more azimuthal angles relative to an optical axis of an optical assembly 106. In an embodiment, the dark-field illuminator 108 is configured to deliver electromagnetic energy at two or more angles of incidence onto two or more focal region locations.

In an embodiment, the plurality of waveguide assemblies 204 include one or more electromagnetic energy waveguides configured to be coupled to at least one electromagnetic energy emitter. For example, in an embodiment, one or more of the plurality of waveguide assemblies 204 include at least one sleeve member 208 configured to receive one or more electromagnetic energy waveguides. In an embodiment, one or more of the plurality of waveguide assemblies 204 include at least one member sleeve 208 configured to receive one or more lenses, polarizers, and electromagnetic energy emitters.

In an embodiment, the plurality of waveguide assemblies 204 are arranged about an aperture 206 in one or more two-dimensional, three dimensional, or n-dimensional (e.g., a time varying configuration) configurations, and the like. For example, in an embodiment, the plurality of waveguide assemblies 204 are axially distributed about an aperture 206. In an embodiment, the plurality of waveguide assemblies 204 are arranged about an aperture 206 in one or more radially symmetric patterns. In an embodiment, the plurality of waveguide assemblies 204 are arranged about an aperture 206 in one or more spherical patterns (see e.g., FIG. 3).

In an embodiment, the plurality of waveguide assemblies 204 are arranged about an aperture 206 in one or more rotationally symmetric patterns. In an embodiment, the plurality of waveguide assemblies 204 are arranged about an aperture 206 in one or more concentric patterns radially symmetric about an axis substantially parallel to the optical axis. In an embodiment, the plurality of waveguide assemblies 204 are arranged about an aperture 206 in one or more concentric patterns rotationally symmetric about an axis substantially parallel to the optical axis. In an embodiment, one or more of the plurality of waveguide assemblies 204 are configured to collimate electromagnetic energy within the aperture 206.

In an embodiment, at least one of the plurality of waveguide assemblies 204 includes at least one polarizer. In an embodiment, at least one of the plurality of waveguide assemblies 204 includes at least one linear-polarizer. In an embodiment, at least one of the plurality of waveguide assemblies 204 includes at least one cross-polarizer. In an embodiment, at least one of the plurality of waveguide assemblies 204 includes at least one circular polarizer. In an embodiment, at least one of the plurality of waveguide assemblies 204 includes at least one adjustable polarizer.

In an embodiment, at least one of the plurality of waveguide assemblies 204 includes at least one lens. In an embodiment, at least one of the plurality of waveguide assemblies 204 includes at least one lens configured to collimate electromagnetic energy emitted by the at least one electromagnetic energy emitter. In an embodiment, at least one of the plurality of waveguide assemblies 204 includes at least one lens configured to focus electromagnetic energy emitted by the at least one electromagnetic energy emitter. In an embodiment, at least one of the plurality of waveguide assemblies 204 includes at least one micro-lens array. In an embodiment, at least one of the plurality of waveguide assemblies 204 includes at least one plano-convex lens. In an embodiment, at least one of the plurality of waveguide assemblies 204 includes at least one aspheric lens.

In an embodiment, at least one of the plurality of waveguide assemblies 204 includes at least one multi-focal lens. In an embodiment, at least one of the plurality of waveguide assemblies 204 includes at least one variable-focus lens. In an embodiment, at least one of the plurality of waveguide assemblies 204 includes at least one liquid lens. In an embodiment, at least one of the plurality of waveguide assemblies 204 includes at least one tunable liquid lens. In an embodiment, at least one of the plurality of waveguide assemblies 204 includes at least one liquid mirror. In an embodiment, at least one of the plurality of waveguide assemblies 204 includes at least one electrowetting-controlled liquid mirror. In an embodiment, the dark-field module 104 is operably coupled to one or more energy-emitting components 112. In an embodiment, the dark-field module 104 is operably coupled to at least one of a laser, a laser diode, or a light-emitting diode. In an embodiment, the dark-field module 104 is operably coupled to at least one of a quantum dot, an organic light-emitting diode, a microcavity light-emitting diode, or a polymer light-emitting diode. In an embodiment, the dark-field module 104 is operably coupled to at least one femtosecond laser.

In an embodiment, the dark-field illuminator 108 includes means for removably attaching the dark-field illuminator 108 to an optical assembly 106. For example, in an embodiment, the dark-field illuminator 108 includes a slip ring 212, a locking member 214, and an adapter 216 for coupling the optical assembly 106 to the dark-field illuminator 108. In an embodiment, the means for removably attaching the dark-field illuminator 108 to an optical assembly 106 includes a coupling structure on the dark-field illuminator 108 that couples to a respective coupling structure on optical assembly 106. For example, in an embodiment, the means for removably attaching the dark-field illuminator 108 to an optical assembly 106 includes a coupling member having a surface defining an inner passageway, the inner passageway sized and dimensioned to friction fit over an outer surface of an optical assembly 106. In an embodiment, the means for removably attaching the dark-field illuminator 108 to an optical assembly 106 includes at least one of a bayonet coupling structure, a friction fit coupling structure, a snap fit coupling structure, or a threaded coupling structure having one or more substructures adapted to coupled to a corresponding bayonet coupling structure, friction fit coupling structure, snap fit coupling structure, or threaded coupling structure on an assembly 112. In an embodiment, the dark-field illuminator 108 is configured to removably attach to an optical assembly 106 by a bayonet coupling, a friction fit coupling, a snap fit coupling, or a threaded coupling. In an embodiment, the dark-field illuminator 108 includes a coupling structure configured to removably attach the dark-field reflected-illumination apparatus to an optical assembly 106. In an embodiment, the coupling structure is configured to removably attach the dark-field reflected-illumination apparatus to the optical assembly 106 by a bayonet coupling, a friction fit coupling, a snap fit coupling, or a threaded coupling.

In an embodiment, the optical assembly 106 includes one or more optical assembly body structures 107 coupled at one end to a sensor component 114 (e.g., a photodetector, an electromagnetic energy sensors, a charged-coupled device, a camera, a spectrometer, and the like), via one or more adapters 218. In an embodiment, the optical assembly 106 includes at least one plano convex lens and at least one lens retention member 220. In an embodiment, the optical assembly 106 is operably coupled to at least one polarizer 222 and at least one polarizer retention member 224. In an embodiment, the optical assembly 106 includes at least retention member 226 configured to secure a lens assembly within an optical assembly body structure 107. In an embodiment, the optical assembly 106 includes at least objective assembly 324.

In an embodiment, the dark-field illuminator 108 includes means 228 for adjusting a dark-field illuminator distance relative to an optical assembly 106 along an axis substantially parallel to an optical axis of the optical assembly 106. In an embodiment, the means 228 for adjusting the dark-field illuminator distance relative to an optical assembly 106 includes a rotatable-adjustment structure 230 sized and dimensioned to coupled to a threaded member 232. In an embodiment, the means 228 for adjusting the dark-field illuminator distance relative to an optical assembly 106 includes a dark-field illuminator securing member 234 operable to constrain rotation or displacement of the dark-field illuminator 108. In an embodiment, the optical assembly 106 includes one or more objectives 236.

In an embodiment, the dark-field illuminator 108 includes a body structure 202 having a plurality of waveguide assemblies 204 and a sensor component 114 including one or more sensors configured to receive scattered electromagnetic energy from an object interrogated by the dark-field illuminator 108. In an embodiment, the plurality of waveguide assemblies 204 includes at least a first electromagnetic energy emitter and a second electromagnetic energy emitter, the second electromagnetic energy emitter having at least one of an illumination intensity, a peak emission wavelength, or a pulse frequency different from the first electromagnetic energy emitter. In an embodiment, the sensor component 114 includes a sensor array for acquiring angle-dependent electromagnetic energy scattering information. In an embodiment, the sensor component 114 includes a sensor array for acquiring wavelength-dependent electromagnetic energy scattering information.

In an embodiment, the dark-field illuminator 108 includes means 228 for adjusting a dark-field illuminator distance relative to an optical assembly 106 along an axis substantially parallel to an optical axis of the optical assembly 106. In an embodiment, the means 228 for adjusting the dark-field illuminator distance relative to an optical assembly 106 includes a rotatable-adjustment structure 232 sized and dimensioned to coupled to a threaded member 230. In an embodiment, the means 228 for adjusting the dark-field illuminator distance relative to an optical assembly 106 includes a dark-field illuminator securing member 234 operable to constrain rotation or displacement of the dark-field illuminator 108.

In an embodiment, the dark-field illuminator 108 includes a plurality of sensors and a plurality of interrogators. In an embodiment, the plurality of sensors is configured to capture scattered electromagnetic energy from a sample interrogated by the dark-field illuminator 108. In an embodiment, each of the plurality of interrogators includes a waveguide assembly 204 including one or more electromagnetic energy waveguides configured to be coupled to at least one energy-emitting component 112, the plurality of interrogators oriented to focus electromagnetic energy onto at least one focal region within the least one aperture 206 at one or more angles of incidence relative to an optical axis of an optical assembly.

In an embodiment, the dark-field illuminator 108 includes means for adjusting an angle of incidence of electromagnetic energy delivered by the dark-field illuminator 108. In an embodiment, the means for adjusting the angle of incidence of electromagnetic energy delivered by the dark-field illuminator 108 includes a computing device operably coupled to at least one of a mechanical-optic component, an electro-optic component, or an acousto-optic component. In an embodiment, the means for adjusting the angle of incidence of electromagnetic energy delivered by the dark-field illuminator 108 includes a computing device operably coupled to at least one of an optical waveguide configured to change an angle of incidence of electromagnetic energy delivered by one or more of the plurality of waveguide assemblies 204. In an embodiment, the means for adjusting the angle of incidence of electromagnetic energy delivered by the dark-field illuminator 108 includes a computing device operably coupled to at least one tunable liquid lens. In an embodiment, the means for adjusting the angle of incidence of electromagnetic energy delivered by the dark-field illuminator 108 includes a computing device operably coupled to at least one optical microprism. In an embodiment, the means 3 for adjusting the angle of incidence of electromagnetic energy delivered by the dark-field illuminator 108 includes a computing device operably coupled to one or more micro-lens-arrays.

In an embodiment, an apparatus 102 is configured to identifying, classifying, differentiating, etc., objects (e.g., cells, bacteria, bacterial diseases, contaminants, and the like). In an embodiment, an apparatus 102 employs spectral learning in identifying, classifying, differentiating, etc., to improve sensitivity and specificity of a diagnosis.

In an embodiment, an apparatus 102 includes an optical assembly 106 having a sample side, a detector side, and an optical axis therethrough; a dark-field illuminator 108 proximate the sample side of the optical assembly 106; and means 228 for adjusting a dark-field illuminator distance relative to an optical assembly 106 along an axis substantially parallel to an optical axis of the optical assembly 106. In an embodiment, an apparatus 102 includes a sensor component 114 configured to capture one or more micrographs associated with the scattered electromagnetic energy from the sample interrogated by the dark-field illuminator. In an embodiment, an apparatus 102 includes a stage assembly configured to secure a sample for analysis. In an embodiment, the dark-field illuminator 108 includes a plurality of waveguide assemblies 204, and a body structure 202 having an aperture 206 aligned along an axis substantially parallel to an optical axis. In an embodiment, the optical assembly 106 is configured to receive scattered electromagnetic energy from a sample interrogated by the dark-field illuminator 108. In an embodiment, an apparatus 102 includes sample stage assembly configured to receive a sample chamber during operation. In an embodiment, a sample stage assembly is configured to position a sample including one or more objects along an x, y, or z direction. In an embodiment, the sample stage assembly includes a stepper motor operably coupled to the dark-field module 104 and configured to positioning a sample chamber based on a tiling protocol.

In an embodiment, the hyperspectral imaging module 110 includes circuitry configured to compare an angular-resolved and spectrally resolved scattering matrix to reference angular-resolved and spectrally resolved hyperspectral information, and classify the object within the at least one focal volume interrogated by the dark-field module 104, based on the comparison. In an embodiment, the hyperspectral imaging module 110 includes circuitry configured to detecting (e.g., assess, calculate, evaluate, determine, gauge, identify, measuring, monitor, quantify, resolve, sense, or the like) spectral information nonlinear multi-harmonic response energy associated with objects within the at least one focal volume interrogated by the dark-field module 104. See, e.g., U.S. Patent Publication No. 2010/0222774 (published Sep. 2, 2010); which is incorporated herein by reference).

In an embodiment, the hyperspectral imaging module 110 includes circuitry configured to compare spectral information and object shape information and identify imaged objects based on the comparison. In an embodiment the hyperspectral imaging module 110 includes circuitry that compares spectral information and object shape information to dimensionality information to identify imaged objects. In an embodiment, the hyperspectral imaging module 110 includes one or more module configured to identify imaged objects using one or more T-test protocols, threshold clustering protocols, etc. In an embodiment, the hyperspectral imaging module 110 includes circuitry configured to classify an object using one or more of morphological information, spatial dimensions information, brightness information, spectral signature information derived from the spectral dimension information, and scattering profile information from the angular dimension.

In an embodiment, the hyperspectral imaging module 110 includes circuitry configured to identify identifying significant objects using at least one of a Clustering protocol or a Learning protocol. For example, in an embodiment, the hyperspectral imaging module 110 includes one or more modules operable to partition angular-resolved and spectrally resolved scattering information into one or more information subsets using at least one of Clustering protocol. In an embodiment, the hyperspectral imaging module 110 includes one or more modules operable to partition angular-resolved and spectrally resolved scattering information into one or more information subsets using at least one Learning protocol. In an embodiment, the hyperspectral imaging module 110 includes circuitry configured to identify identifying significant objects using at least one of a Fuzzy C-Means Clustering protocol, a Graph-Theoretic protocol, a Hierarchical Clustering protocol, a K-Means Clustering protocol, a Local-ity-Sensitive Hashing protocol, a Mixture of Gaussians protocol, a Model-Based Clustering protocol, a Cluster-Weighted Modeling protocol, an Expectations-Maximization protocol, a Principal Components Analysis protocol, and a Partitioning protocol.

Figure 5:
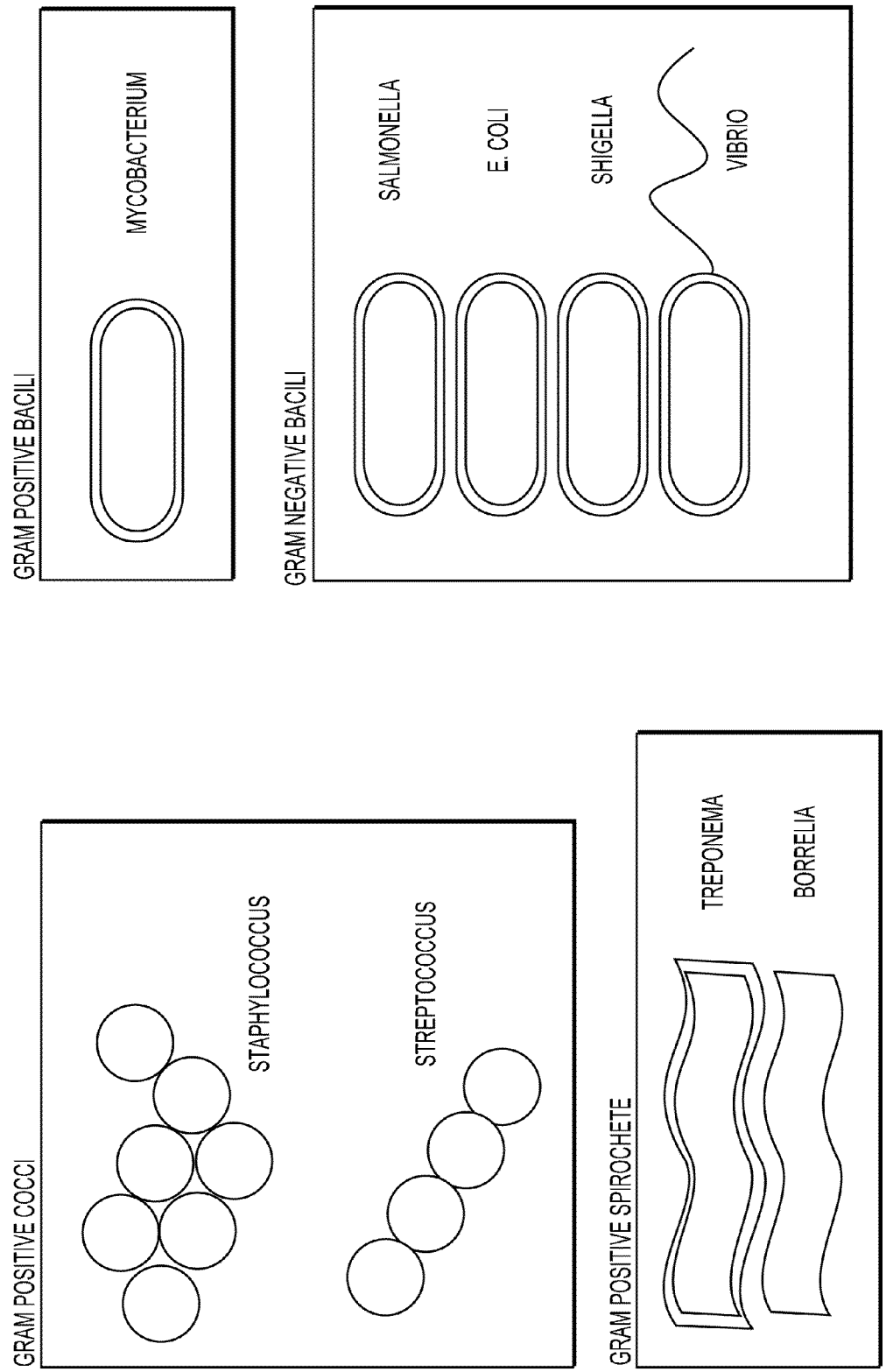
FIG. 5 shows an information structure according to one embodiment.

In an embodiment, the hyperspectral imaging module 110 is operably coupled to one or more object classification modules. For example, in an embodiment, the hyperspectral imaging module 110 is operably coupled to one or more linear algebra, fuzzy logic, neural network, or regression object classification modules. In an embodiment, the hyperspectral imaging module 110 is operably coupled to one or more simple threshold principal component analysis, linear discriminant analysis, fuzzy c-mean clustering, regressions, and least-square fits classification modules. Referring to FIG. 5, different bacteria can have one or more different shapes (e.g., coccus, spirochete, bacillus, etc.), different alignments (e.g., clusters, strips, aggregates, etc.), different cell membrane structures (e.g., gram positive, gram negative, etc.), and the like, which can be used for identification of pathogenic species. In an embodiment, the hyperspectral imaging module 110 is operably coupled to one or more pathogenic species classification modules.

Figure 4:
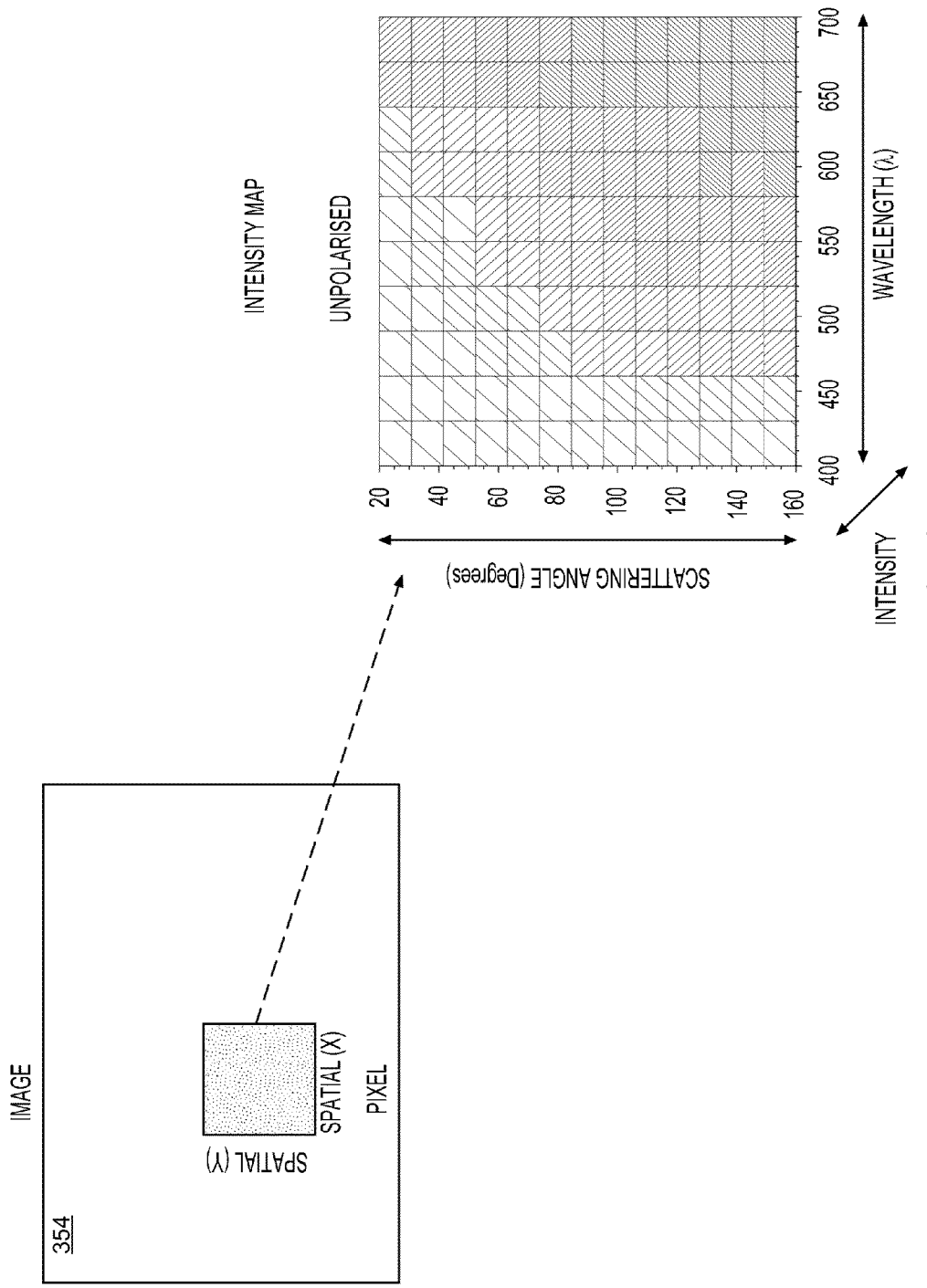
FIG. 4 shows a perspective view of information structures according to one embodiment.

In an embodiment, hyperspectral imaging module 110 is operably coupled to the dark-field module 104, and is configured to generate an angular-resolved and spectrally resolved scattering matrix based on the one or more dark-field micrographs of an object. In an embodiment, the hyperspectral imaging module 110 includes circuitry configured to generate spatially resolved image of an object interrogated by the dark-field interrogation stimulus. In an embodiment, the hyperspectral imaging module 110 includes circuitry configured to generate one or more spatially resolved images of an object interrogated by the dark-field interrogation stimulus. In an embodiment, the hyperspectral imaging module 110 includes circuitry configured to generate a pixel by pixel, wavelength versus illumination angle intensity map for an object interrogated by the dark-field interrogation stimulus. Referring to FIG. 4, in an embodiment, the hyperspectral imaging module 110 includes circuitry configured to generate four-dimensional angle-resolved multispectral information, including intensity mapped in two dimensions (scattering angle versus wavelength) for every x-y pixel of a dark-field images 354. In an embodiment, the hyperspectral imaging module 110 includes circuitry configured to generate virtual representation of angular-resolved and spectrally resolved scattering information associated with one or more micrographs of an object.

Referring to FIGS. 1-3, in an embodiment, the system 100 includes a dark-field module 104, an optical assembly 106, a dark-field illuminator 108, and hyperspectral imaging module 110. In an embodiment, the dark-field module 104 includes one or more sensors operable to acquire one or more dark-field micrographs associated with scattered electromagnetic energy from an object interrogated by the dark-field interrogation stimulus. In an embodiment, the dark-field illuminator 108 is configured to deliver a dark-field interrogation stimulus onto at least one focal region, at one or more angles of incidence relative to an optical axis of an optical assembly 106. In an embodiment, hyperspectral imaging module 110 is configured to generate angular-resolved and spectrally resolved scattering information responsive to dark-field detection of an object interrogated by the dark-field interrogation stimulus.

In an embodiment, the systems 100, apparatus 102, modules, etc., and the other devices disclosed herein operate in a networked environment using connections to one or more remote computing devices (e.g., a common network node, a network computer, a network node, a peer device, a personal computer, a router, a server, a tablet PC, a tablet, etc.) and typically includes many or all of the elements described above. In an embodiment, the connections include connections to a local area network (LAN), a wide area network (WAN), or other networks. In an embodiment, the connections include connections to one or more enterprise-wide computer networks, intranets, and the Internet. In an embodiment, the systems 100, apparatus 102, modules, or the like operate in a cloud computing environment including one or more cloud computing systems (e.g., private cloud computing systems, public cloud computing systems, hybrid cloud computing systems, or the like).

In an embodiment, the system 100 includes an object classification module 402. In an embodiment, the object classification module 402 is configured to compare the angular-resolved and spectrally resolved scattering matrix to reference angular-resolved and spectrally resolved hyperspectral information, and to generate classification information associated with objects imaged in the one or more dark-field micrographs based on the comparison. For example, in an embodiment, the object classification module 402 includes circuitry operable to compare the angular-resolved and spectrally resolved scattering matrix to reference angular-resolved and spectrally resolved hyperspectral information, and to generate classification information associated with objects imaged in the one or more dark-field micrographs based on the comparison.

In an embodiment, the object classification module 402 is operable to compare angular-resolved and spectrally resolved scattering matrices to angular-resolved reference objects information and to generate classification information based on the comparison. In an embodiment, the object classification module 402 is operable to compare angular-resolved and spectrally resolved scattering matrices to spatially resolved reference objects information and to generate classification information based on the comparison. In an embodiment, the object classification module 402 is operable to generate object classification information based on the comparison. In an embodiment, the object classification module 402 is operable to classify imaged objects based on generated principal components information. In an embodiment, the object classification module 402 is operable to generate object identification information based on principal components information. In an embodiment, the object classification module 402 is operable to generate object identification information based on discrimination filter information. In an embodiment, the system 100 includes an object classification module 402 having circuitry operable to activate at least one of an object identification mode, an object classification mode, and an object characterization mode.

In an embodiment, systems 100 is configured for automated identification, classification, differentiation, etc., of objects (e.g., particles, biological samples, bacteria, cell membrane structures, etc.) identifying significant objects from the field using spatial image processing methodologies such as a T-test or threshold test. Clips of significant objects could then be analyzed for scatter characteristics. Selective identification could use discriminating filters based on both morphology and scattering information.

In an embodiment, the system 100 includes an illumination angle controller operably coupled to the dark-field illuminator 108, the illumination angle controller operable to modulate an angle of incidence of electromagnetic energy delivered by the dark-field illuminator 108. In an embodiment, the system 100 includes an aperture control module operably coupled to an aperture device, the aperture control module having circuitry configured to modulate an effective numerical aperture associated with a collection zone of scattered electromagnetic energy from an object interrogated by the dark-field interrogation stimulus. In an embodiment, the system 100 includes an illumination-collection separation control module operably coupled to dark-field module 104 and an aperture control module, the illumination-collection separation control module including circuitry configured to vary an illumination-collection spacing, bounded in part by the electromagnetic energy delivered by the dark-field illuminator 108 and a collection zone, by actuating at least one of the dark-field module 104 and an aperture control module.

In an embodiment, the system 100 includes a dark-field illuminator 108 operably coupled to an optical assembly 106, a dark-field illuminator 108 having a plurality of energy emitters. In an embodiment, the plurality of energy emitters is configured to focus electromagnetic energy onto at least one focal region, at one or more angles of incidence relative to an optical axis of the optical assembly 106. In an embodiment, the system 100 includes a sample chamber configured to receive a sample including one or more objects.

In an embodiment, the system 100 includes a sensor component 114 that forms part of hyperspectral imaging module 110. In an embodiment, the hyperspectral imaging module 110 is configured to modulate an angle of incidence of electromagnetic energy delivered by the dark-field illuminator 108. In an embodiment, the hyperspectral imaging module 110 is configured to acquire one or more angular-resolved dark-field images of at least a portion of an object at different fields of view. In an embodiment, the hyperspectral imaging module 110 is configured to and generate angular-resolved and spectrally resolved hyperspectral information based on the one or more angular-resolved dark-field image.

In an embodiment, the system 100 includes an object classification module 402 having circuitry operable to compare the angular-resolved and spectrally resolved hyperspectral information to reference angular-resolved and spectrally resolved hyperspectral information. In an embodiment, the system 100 includes an object classification module 402 having circuitry operable to classify objects based on the comparison.

In an embodiment, the object classification module 402 is operable to compare the angular-resolved and spectrally resolved hyperspectral information to one or more reference scattering array images. In an embodiment, the object classification module 402 is operable to compare the angular-resolved and spectrally resolved hyperspectral information to one or more spatially resolved reference object images. In an embodiment, the object classification module 402 is operable to compare the angular-resolved and spectrally resolved hyperspectral information to one or more spatially resolved reference object images.

Referring to FIG. 1, in an embodiment, a hyperspectral image sensor is operably coupled to one or more modules having circuitry configured to generate four-dimensional angle-resolved dark-field images of the object. In an embodiment, the hyperspectral image sensor is operably coupled to one or more modules having circuitry configured to generate spatially resolved, angle versus wavelength versus intensity information of the object. In an embodiment, the hyperspectral image sensor is operably coupled to one or more modules having circuitry configured to generate angle versus wavelength versus intensity information for a plurality of pixels.

In an embodiment a dark-field object classification apparatus includes an illumination-angle controller. In an embodiment, the illumination-angle controller is operable to vary an angle of incidence of electromagnetic energy delivered by a dark-field illuminator 108. In an embodiment, the dark-field illuminator 108 is oriented to focus electromagnetic energy onto at least one focal region, at one or more angles of incidence relative to an optical axis of an optical assembly. In an embodiment a dark-field object classification apparatus includes an illumination-wavelength controller. In an embodiment, the angle controller is operable to vary a peak emission wavelength, an ON-pulse duration, an OFF-pulse duration, a pulse frequency, etc., of electromagnetic energy.

In an embodiment a dark-field object classification apparatus includes an aperture controller operably coupled to an aperture device, the aperture controller operable to modulate an effective numerical aperture associated with a collection zone of scattered electromagnetic energy from the object interrogated by the electromagnetic energy delivered by the dark-field illuminator 108. In an embodiment a dark-field object classification apparatus includes a hyperspectral image controller having circuitry configured to acquire one or more angular-resolved dark-field images of the object. In an embodiment a dark-field object classification apparatus includes a hyperspectral image controller having circuitry configured to generate an angular-resolved and spectrally resolved scattering matrix based on the one or more angular-resolved dark-field images. In an embodiment a dark-field object classification apparatus includes a hyperspectral image controller having circuitry configured to generate object classification information based on the comparison.

Referring to FIGS. 3-7, in an embodiment, during operation, the system 100 is configured to classify objects in a sample based on hyperspectral angle-resolved scattering (HARS) measurements. In an embodiment, the system 100 includes circuitry configured to acquire hyperspectral or multispectral dark-field images, of the same field of view of the sample, for a plurality of different dark-field aperture settings. In an embodiment, the different dark-field apertures allow angle-resolved information of an object's scattering profile. In an embodiment, during operation, the system 100 acquires a spectral and angular-resolved map for a plurality of spatial pixels of an image. For example, in an embodiment, during operation, the dark-field illuminator 108 illuminates a sample from a number of different angles, at different wavelengths. In an embodiment, the dark-field module 104 includes circuitry configured to generate two-dimensional scatter spectra for a plurality of a sample image.

Figure 6:
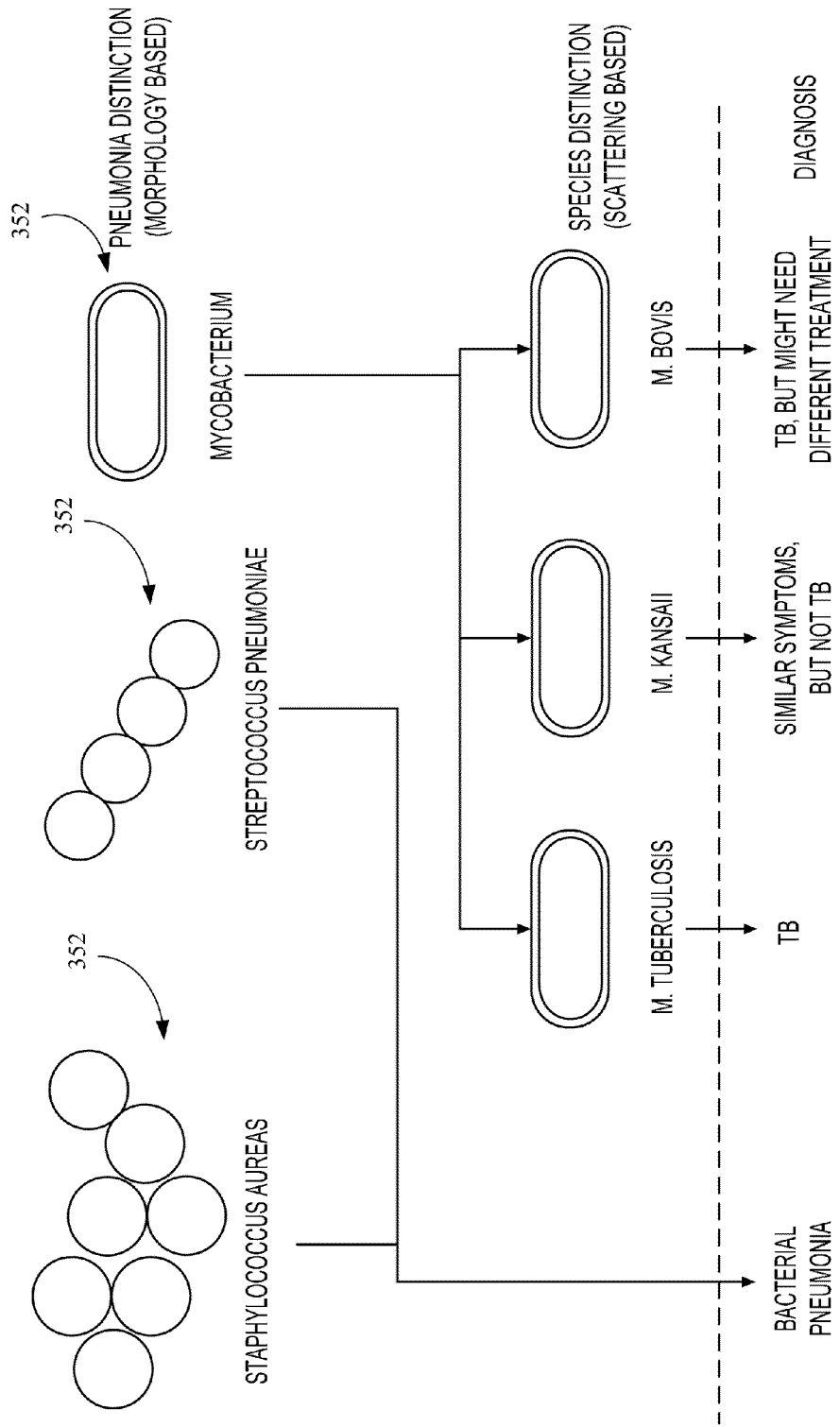
FIG. 6 shows according to one embodiment.

Referring to FIG. 6, in an embodiment, the apparatus 102 includes one or more module configured to interrogate objects 352, and to identify, classify, differentiate, etc., interrogated objects (e.g., particles, biological samples, bacteria, cell membrane structures, etc.) using both morphological information and scattering information.

Figure 7:
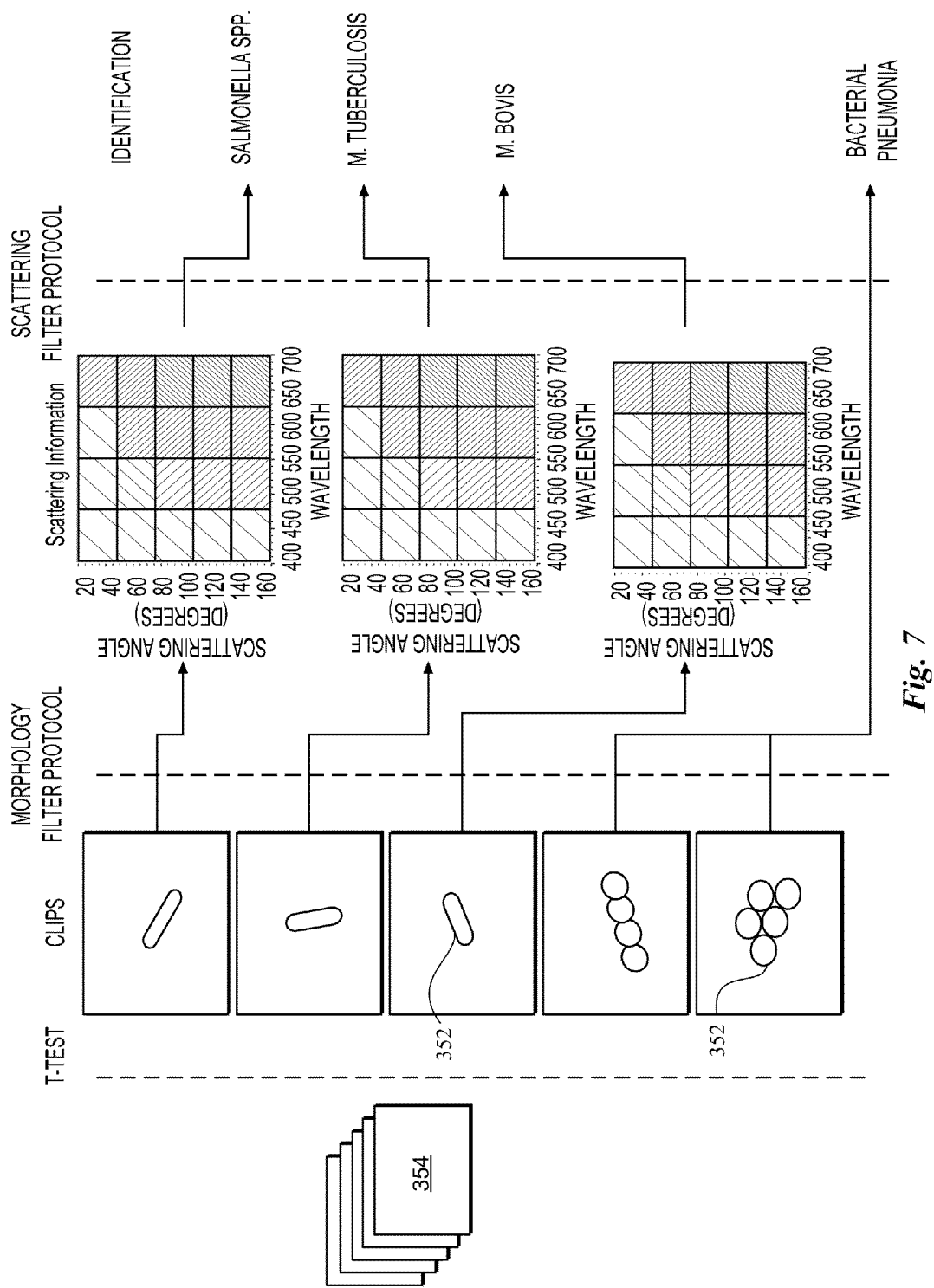
FIG. 7 shows a schematic diagram of an article of manufacture according to one embodiment.

Referring to FIG. 7, in an embodiment, the system 100 includes an apparatus 102 having one or more modules configured to acquire one or more dark-field images 354 of objects 352. In an embodiment, the apparatus 102 includes one or more modules operably coupled to circuitry configured to generate significant objects information from within a field of view, via one or spatial image processing protocols such as a T-test protocols, threshold test protocols, and the like. In an embodiment, generating significant objects information includes generating one or more clips of significant objects. In an embodiment, the apparatus 102 includes one or more modules operably coupled to circuitry configured to classifying objects 352 based on one or more discriminating filters protocols. In an embodiment, classifying objects 352 based on one or more discriminating filters protocols includes classifying objects based on morphology filters protocols and scattering filters protocols. In an embodiment, the apparatus 102 includes one or more modules operably coupled to circuitry configured to generate a diagnosis based on at least one datum from the significant objects information.

Referring to FIG. 8, in an embodiment, an article of manufacture 802 includes a non-transitory signal-bearing medium bearing one or more instructions for focusing electromagnetic energy onto at least one focal region, at one or more angles of incidence relative to an optical axis of an optical assembly. In an embodiment, an article of manufacture 802 includes a non-transitory signal-bearing medium bearing one or more instructions for acquiring one or more angular-resolved and spectrally resolved dark-field images of the object. In an embodiment, an article of manufacture 802 includes a non-transitory signal-bearing medium bearing one or more instructions for generating angular-resolved and spectrally resolved hyperspectral information representation based on the one or more angular-resolved and spectrally resolved dark-field images of the object. In an embodiment, an article of manufacture 802 includes a non-transitory signal-bearing medium bearing one or more instructions for classifying objects in the object responsive to a comparison of the angular-resolved and spectrally resolved hyperspectral information representation to reference angular-resolved and spectrally resolved hyperspectral information. In an embodiment, an article of manufacture 802 includes a non-transitory signal-bearing medium bearing one or more instructions for generating a virtual representation of at least one datum associated with an angular-resolved and spectrally resolved dark-field image of the object. In an embodiment, an article of manufacture 802 includes a non-transitory signal-bearing medium bearing one or more instructions for varying an illumination-collection spacing by varying at least one of an illumination angle of incidence or a collection aperture dimension based on a detected contrast differential. In an embodiment, an article of manufacture 802 includes a non-transitory signal-bearing medium bearing one or more instructions for generating object identification information based on principal components information. In an embodiment, an article of manufacture 802 includes a non-transitory signal-bearing medium bearing one or more instructions for generating object identification information based on discrimination filter information.

Referring to FIG. 9, in an embodiment, an article of manufacture 902 includes a non-transitory signal-bearing medium bearing one or more instructions for acquiring a plurality of hyperspectral dark-field images of a biological object at a first field of view and a second field of view, for one or more dark-field apertures at each of the first field of view and the second field of view. In an embodiment, an article of manufacture 902 includes a non-transitory signal-bearing medium bearing one or more instructions for classifying the biological object based on a comparison of an angular-resolved and spectrally resolved scattering matrix to reference angular-resolved and spectrally resolved information.

In an embodiment, an article of manufacture 902 includes a non-transitory signal-bearing medium bearing one or more instructions for generating an angular-resolved and spectrally resolved scattering matrix based on the plurality of hyperspectral dark-field images at the first field of view. In an embodiment, an article of manufacture 902 includes a non-transitory signal-bearing medium bearing one or more instructions for generating an angular-resolved and spectrally resolved scattering matrix based on the plurality of hyperspectral dark-field images at the second field of view. In an embodiment, an article of manufacture 902 includes a non-transitory signal-bearing medium bearing one or more instructions for generating an angular-resolved and spectrally resolved scattering matrix based on the plurality of hyperspectral dark-field images at the first field of view or the second field of view. In an embodiment, an article of manufacture 902 includes a non-transitory signal-bearing medium bearing one or more instructions for generating hyperspectral information based on the plurality of hyperspectral dark-field images at the first field of view or the second field of view. In an embodiment, an article of manufacture 902 includes a non-transitory signal-bearing medium bearing one or more instructions for classifying the biological object based on a comparison of the angular-resolved and spectrally resolved hyperspectral information to reference angular-resolved and spectrally resolved dark-field information. In an embodiment, an article of manufacture 902 includes a non-transitory signal-bearing medium bearing one or more instructions for generating registration information for real-time registering a biological object relative to a reference location.

Referring to FIG. 10, in an embodiment, an article of manufacture 1002 includes a non-transitory signal-bearing medium bearing one or more instructions for generating an angular-resolved map for each of a plurality of pixels of a dark-field micrograph of at least a portion of an object under test. In an embodiment, an article of manufacture 1002 includes a non-transitory signal-bearing medium bearing one or more instructions for generating angular-resolved and spectrally resolved hyperspectral information based on a plurality of angular-resolved maps. In an embodiment, an article of manufacture 1002 includes a non-transitory signal-bearing medium bearing one or more instructions for classifying the biological sample based on a comparison of the angular-resolved and spectrally resolved hyperspectral information to reference angular-resolved and spectrally resolved information.

Referring to FIG. 11, in an embodiment, an article of manufacture 1102 includes a non-transitory signal-bearing medium bearing one or more instructions for acquiring hyperspectral dark-field images or multispectral dark-field images, for at least a first field of view, and for at least a first dark-field aperture and a second dark-field aperture, the second dark-field aperture different from the first dark-field aperture. In an embodiment, an article of manufacture 1102 includes a non-transitory signal-bearing medium bearing one or more instructions for generating classification information associated with the object under test based on a comparison of the hyperspectral dark-field images or the multispectral dark-field images of the object to reference hyperspectral dark-field information or reference multispectral dark-field information.

FIG. 12 shows an example of a method 1200 for classifying objects. At 1210, the method 1200 includes focusing electromagnetic energy onto at least one focal region, at one or more angles of incidence relative to an optical axis of an optical assembly. At 1220, the method 1200 includes acquiring one or more angular-resolved and spectrally resolved dark-field images of the object. At 1230, the method 1200 includes generating angular-resolved and spectrally resolved hyperspectral information representation based on the one or more angular-resolved and spectrally resolved dark-field images of the object. At 1240, the method 1200 includes classifying objects responsive to a comparison of the angular-resolved and spectrally resolved hyperspectral information representation to reference angular-resolved and spectrally resolved hyperspectral information. At 1250, the method 1200 includes generating a virtual representation of an object classification responsive to a comparison of the angular-resolved and spectrally resolved hyperspectral information representation to reference angular-resolved and spectrally resolved hyperspectral information. At 1260, the method 1200 includes generating a virtual representation of at least one angular-resolved and spectrally resolved dark-field image of the object. At 1270, the method 1200 includes varying an illumination-collection spacing by varying at least one of an illumination angle of incidence or a collection aperture dimension based on a detected contrast differential. At 1280, the method 1200 includes varying one of the illumination angle or the collection aperture dimension while maintaining a substantially fixed illumination-collection spacing.

FIG. 13 shows an example of a method 1300. At 1310, the method 1300 includes acquiring a plurality of hyperspectral dark-field images of a biological object, for one or more dark-field apertures at each of the first field of view at a first field of view. At 1320, the method 1300 includes classifying the biological object based on a comparison of an angular-resolved and spectrally resolved scattering matrix to reference angular-resolved and spectrally resolved information. At 1330, the method 1300 includes generating an angular-resolved and spectrally resolved scattering matrix based on the plurality of hyperspectral dark-field images at the first field of view. At 1340, the method 1300 includes generating an angular-resolved and spectrally resolved scattering matrix based on the plurality of hyperspectral dark-field images at the first field of view. At 1350, the method 1300 includes generating hyperspectral information based on the plurality of hyperspectral dark-field images at the first field of view. At 1360, the method 1300 includes classifying the biological object based on a comparison of the angular-resolved and spectrally resolved hyperspectral information to reference angular-resolved and spectrally resolved dark-field information. At 1370, the method 1300 includes acquiring a plurality of hyperspectral dark-field images of a biological subject at a second field of view, for one or more dark-field apertures at the second field of view. At 1380, the method 1300 includes acquiring a plurality of hyperspectral dark-field images of a biological subject at a third field of view, for one or more dark-field apertures at the third field of view. In an embodiment, the method 1300 includes generating a diagnosis based on at least one datum from the objects scattering information.

Referring to FIG. 14, in an embodiment, an article of manufacture 1402 includes a non-transitory signal-bearing medium bearing one or more instructions for acquiring a plurality of hyperspectral dark-field images of a biological subject, for at least a first field of view and a second field of view, for one or more dark-field apertures at each of the first field of view and the second field of view. In an embodiment, an article of manufacture 1402 includes a non-transitory signal-bearing medium bearing one or more instructions for generating an angular-resolved and spectrally resolved hyperspectral dark-field information based on the plurality of hyperspectral dark-field images. In an embodiment, an article of manufacture 1402 includes a non-transitory signal-bearing medium bearing one or more instructions for classifying the biological object based on a comparison of the angular-resolved and spectrally resolved hyperspectral information to reference angular-resolved and spectrally resolved dark-field information.

The claims, description, and drawings of this application may describe one or more of the instant technologies in operational/functional language, for example as a set of operations to be performed by a computer. Such operational/functional description in most instances can be specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions are representative of static or sequenced specifications of various hardware elements. This is true because tools available to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits-)—are generators of static or sequenced specifications of various hardware configurations. This fact is sometimes obscured by the broad term "software," but, as shown by the following explanation, what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, (as of Jun. 5, 2012, 21:00 GMT). In order to facilitate human comprehension, in many instances, high-level programming languages resemble or even share symbols with natural languages. See, e.g., Wikipedia, Natural language, (as of Jun. 5, 2012, 21:00 GMT).

It has been argued that because high-level programming languages use strong abstraction (e.g., that they may resemble or share symbols with natural languages), they are therefore a "purely mental construct." (e.g., that "software"—a computer program or computer-programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In an embodiment, if a high-level programming language is the tool used to implement a technical disclosure in the form of functions/operations, it can be understood that, far from being abstract, imprecise, "fuzzy," or "mental" in any significant semantic sense, such a tool is instead a near incomprehensibly precise sequential specification of specific computational-machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory devices, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, (as of Jun. 5, 2012, 21:04 GMT).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. Accordingly, any such operational/functional technical descriptions may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, it can be recognizes that a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

At least a portion of the devices or processes described herein can be integrated into an information processing system. An information processing system generally includes one or more of a system unit housing, a video display device, memory, such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), or control systems including feedback loops and control motors (e.g., feedback for detecting position or velocity, control motors for moving or adjusting components or quantities). An information processing system can be implemented utilizing suitable commercially available components, such as those typically found in data computing/communication or network computing/communication systems.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes or systems or other technologies described herein can be effected (e.g., hardware, software, firmware, etc., in one or more machines or articles of manufacture), and that the preferred vehicle will vary with the context in which the processes, systems, other technologies, etc., are deployed. For example, if an implementer determines that speed and accuracy are paramount, the implementer may opt for a mainly hardware or firmware vehicle; alternatively, if flexibility is paramount, the implementer may opt for a mainly software implementation that is implemented in one or more machines or articles of manufacture; or, yet again alternatively, the implementer may opt for some combination of hardware, software, firmware, etc. in one or more machines or articles of manufacture. Hence, there are several possible vehicles by which the processes, devices, other technologies, etc., described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. In an embodiment, optical aspects of implementations will typically employ optically-oriented hardware, software, firmware, etc., in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable, physically interacting components, wirelessly interactable, wirelessly interacting components, logically interacting, logically interactable components, etc.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components, or inactive-state components, or standby-state components, unless context requires otherwise.

The foregoing detailed description has set forth various embodiments of the devices or processes via the use of block diagrams, flowcharts, or examples. Insofar as such block diagrams, flowcharts, or examples contain one or more functions or operations, it will be understood by the reader that each function or operation within such block diagrams, flowcharts, or examples can be implemented, individually or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A hyperspectral imaging system, comprising:
   a dark-field module including
   an optical assembly coupled to a lens and including an illumination-wavelength controller, and
   a dark-field illuminator operable to deliver a dark-field interrogation stimulus onto at least one focal region, at one or more angles of incidence relative to an optical axis of the optical assembly,
   the dark-field module having circuitry including one or more sensors operable to acquire one or more dark-field micrographs associated with scattered electromagnetic energy from an object resulting from the dark-field interrogation stimulus;
   a hyperspectral imaging module operably coupled to the dark-field module and having circuitry configured to generate an angular-resolved and spectrally resolved scattering matrix based on the one or more dark-field micrographs of the object; and
   an object classification module having circuitry operable to compare the angular-resolved and spectrally resolved scattering matrix to reference angular-resolved and spectrally resolved hyperspectral information, and
   generate classification information associated with objects imaged in the one or more dark-field micrographs based on the comparison.

2. The hyperspectral imaging system of claim 1, wherein the object classification module is operable to compare the angular-resolved and spectrally resolved scattering matrix to angular-resolved reference objects information and to generate classification information based on the comparison.

3. The hyperspectral imaging system of claim 1, wherein the object classification module is operable to compare the angular-resolved and spectrally resolved scattering matrix to spatially resolved reference objects information and to generate classification information based on the comparison.

4. The hyperspectral imaging system of claim 1, wherein the object classification module is operable to generate object classification information based on the comparison.

5. The hyperspectral imaging system of claim 1, wherein the object classification module is operable to generate principal components information.

6. The hyperspectral imaging system of claim 1, wherein the object classification module is operable to generate object identification information based on principal components information.

7. The hyperspectral imaging system of claim 1, wherein the object classification module is operable to generate object identification information based on discrimination filter information.

8. The hyperspectral imaging system of claim 1, further comprising:
   an object classification module having circuitry operable to activate at least one of an object identification mode, an object classification mode, and an object characterization mode.

9. The hyperspectral imaging system of claim 1, wherein the hyperspectral imaging module includes circuitry configured to generate spatially resolved image of an object interrogated by the dark-field interrogation stimulus.

10. The hyperspectral imaging system of claim 1, wherein the hyperspectral imaging module includes circuitry configured to generate one or more spatially resolved images of an object interrogated by the dark-field interrogation stimulus.

11. The hyperspectral imaging system of claim 1, wherein the hyperspectral imaging module includes circuitry configured to generate a wavelength versus illumination angle intensity map for an object interrogated by the dark-field interrogation stimulus.

12. The hyperspectral imaging system of claim 1, further comprising:
an illumination angle controller operably coupled to the dark-field illuminator, the illumination angle controller operable to modulate an angle of incidence of electromagnetic energy delivered by the dark-field illuminator.

13. The hyperspectral imaging system of claim 1, further comprising:
an aperture control module operably coupled to an aperture device, the aperture control module having circuitry configured to modulate an effective numerical aperture associated with a collection zone of scattered electromagnetic energy from an object interrogated by the dark-field interrogation stimulus.

14. The hyperspectral imaging system of claim 1, further comprising:
an illumination-collection separation control module operably coupled to dark-field module and an aperture control module, the illumination-collection separation control module including circuitry configured to vary an illumination-collection spacing, bounded in part by the electromagnetic energy delivered by the dark-field illuminator and a collection zone, by actuating at least one of the dark-field module and an aperture control module.

15. The hyperspectral imaging system of claim 1, further comprising:
a sample chamber configured to receive a sample including one or more objects.

16. A hyperspectral imaging apparatus, comprising:
an optical assembly including an illumination-wavelength controller;
a dark-field illuminator operably coupled to the optical assembly, the dark-field illuminator having a plurality of energy emitters configured to focus electromagnetic energy onto at least one focal region, at one or more angles of incidence relative to an optical axis of the optical assembly;
a hyperspectral image sensor operably coupled to the dark-field illuminator, the hyperspectral image sensor having circuitry configured to
modulate an angle of incidence of electromagnetic energy delivered by the dark-field illuminator,
acquire one or more angular-resolved dark-field images of at least a portion of an object at different fields of view, and
generate angular-resolved and spectrally resolved hyperspectral information based on the one or more angular-resolved dark-field image; and
an object classification module having circuitry operable to compare the angular-resolved and spectrally resolved hyperspectral information to reference angular-resolved and spectrally resolved hyperspectral information, and classify objects based on the comparison.

17. The hyperspectral imaging apparatus of claim 16, wherein the object classification module is operable to compare the angular-resolved and spectrally resolved hyperspectral information to one or more reference scattering array images.

18. The hyperspectral imaging apparatus of claim 16, wherein the object classification module is operable to compare the angular-resolved and spectrally resolved hyperspectral information to one or more spatially resolved reference object images.

19. The hyperspectral imaging apparatus of claim 16, wherein the hyperspectral image sensor is operably coupled to one or more modules having circuitry configured to generate four-dimensional angle-resolved dark-field images of the object.

20. The hyperspectral imaging apparatus of claim 16, wherein the hyperspectral image sensor is operably coupled to one or more modules having circuitry configured to generate spatially resolved, angle versus wavelength versus intensity information of the object.

21. The hyperspectral imaging apparatus of claim 16, wherein the hyperspectral image sensor is operably coupled to one or more modules having circuitry configured to generate angle versus wavelength versus intensity information for a plurality of pixels.

22. An article of manufacture, comprising:
a non-transitory signal-bearing medium bearing:
one or more instructions for focusing electromagnetic energy onto at least one focal region, at one or more angles of incidence relative to an optical axis of an optical assembly including an illumination-wavelength controller;
one or more instructions for acquiring one or more angular-resolved and spectrally resolved dark-field images of the object;
one or more instructions for generating angular-resolved and spectrally resolved hyperspectral information representation based on the one or more angular-resolved and spectrally resolved dark-field images of the object; and
one or more instructions for classifying objects in the object responsive to a comparison of the angular-resolved and spectrally resolved hyperspectral information representation to reference angular-resolved and spectrally resolved hyperspectral information.

23. The article of manufacture of claim 22, further comprising:
one or more instructions for generating a virtual representation of at least one datum associated with an angular-resolved and spectrally resolved dark-field image of the object.

24. The article of manufacture of claim 22, further comprising:
one or more instructions for varying an illumination-collection spacing by varying at least one of an illumination angle of incidence or a collection aperture dimension based on a detected contrast differential.

25. The article of manufacture of claim 22, further comprising:
one or more instructions for generating object identification information based on principal components information.

26. The article of manufacture of claim 22, further comprising:
one or more instructions for generating object identification information based on discrimination filter information.

27. A dark-field object classification apparatus, comprising:
an illumination-angle controller operable to modulate an angle of incidence of electromagnetic energy delivered by a dark-field illuminator, the dark-field illuminator oriented to focus electromagnetic energy onto at least one focal region, at one or more angles of incidence relative to an optical axis of an optical assembly including an illumination-wavelength controller;
an aperture controller operably coupled to an aperture device, the aperture controller operable to modulate an effective numerical aperture associated with a collection zone of scattered electromagnetic energy from the object interrogated by the electromagnetic energy delivered by the dark-field illuminator; and
a hyperspectral image controller having circuitry configured to
acquire one or more angular-resolved dark-field images of the object,
generate an angular-resolved and spectrally resolved scattering matrix based on the one or more angular-resolved dark-field images,
compare the angular-resolved and spectrally resolved scattering matrix to reference angular-resolved and spectrally resolved hyperspectral information, and
generate object classification information based on the comparison.

* * * * *